(12) United States Patent
Fusaka

(10) Patent No.: US 8,470,738 B2
(45) Date of Patent: *Jun. 25, 2013

(54) PYRIDAZINONE COMPOUND AND HERBICIDE CONTAINING THE SAME

(75) Inventor: Takafumi Fusaka, Kobe (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 455 days.

This patent is subject to a terminal disclaimer.

(21) Appl. No.: 12/733,664

(22) PCT Filed: Sep. 12, 2008

(86) PCT No.: PCT/JP2008/066918
§ 371 (c)(1),
(2), (4) Date: Mar. 12, 2010

(87) PCT Pub. No.: WO2009/035150
PCT Pub. Date: Mar. 19, 2009

(65) Prior Publication Data
US 2010/0216642 A1 Aug. 26, 2010

(30) Foreign Application Priority Data
Sep. 14, 2007 (JP) ................................. 2007-239162

(51) Int. Cl.
C07D 237/16 (2006.01)
A01N 43/58 (2006.01)
(52) U.S. Cl.
USPC ........................... 504/238; 544/240; 544/224
(58) Field of Classification Search
USPC ........ 544/224, 238; 514/247, 252.01; 504/238
See application file for complete search history.

(56) References Cited

U.S. PATENT DOCUMENTS

| 5,097,028 A | 3/1992 | Weissmüller et al. |
| 6,307,047 B1 | 10/2001 | Black et al. |
| 2012/0028988 A1* | 2/2012 | Sakamoto et al. ....... 514/252.03 |

FOREIGN PATENT DOCUMENTS

| CN | 1676518 | 10/2005 |
| JP | 3-58974 | 3/1991 |
| JP | 11-152273 | 6/1999 |
| WO | 2005/007632 A1 | 1/2005 |
| WO | 2005/077914 A1 | 8/2005 |
| WO | 2005/077915 A1 | 8/2005 |
| WO | 2006/052962 A2 | 5/2006 |
| WO | 2006/052962 A3 | 5/2006 |
| WO | WO 2007119434 * | 3/2007 |
| WO | 2007/119434 | 10/2007 |

OTHER PUBLICATIONS

Washington State, Dept of Transport., 2006.*
Vincent, et al., Mycologia, 80(5), 1988, 673-678.*
Palumbo, Review of New Insecticides, 2001, U. of Arizona.*
Stevenson, et al., J. Het. Chem. (2005), 42(3), 427-435.*
International Preliminary Report on Patentability issued Mar. 16, 2010 in corresponding International (PCT) Application No. PCT/JP2008/066918.
Maes, B. U. W. et al., "Suzuki reactions on chloropyridazinones: an easy approach towards arylated 3(2H)-pyridazinones", Tetrahedron 57, pp. 1323-1330, 2001.
Riedl, Z. et al., "Synthesis of new pyridazino[4,5-c]isoquinolinones by Suzuki cross-coupling reaction", Tetrahedron 58, pp. 5645-5650, 2002.
Maes, B. U.W. et al., "Synthesis of 4-aryl-5-hydroxy- and 5-aryl-4-hydroxypyrridazin-3(2H)-ones and their use in the preparation of 4,5-diarylpyrridazin-3(2H)-ones and hitherto unknown isochromeno[3,4-d]pyridazinediones", Tetrahedron 58, pp. 9713-9721, 2002.
Tapolcsányi, P. et al., "Synthesis of the dibenzo[f,h]phthalazine and dibenzo[f,h]cinnoline skeleton via a 'Suzuki-Pd-catalyzed intramolecular arylation' and a 'Suzuki-Pschore ' approach", Tetrahedron 59, pp. 5919-5926, 2003.
Cho, S. et al., "Suzuki-Miyaura coupling reaction of aryl chlorides using di(2,6-dimethylmorpholino)phenylphosphine as ligand", Tetrahedron 63, pp. 1345-1352, 2007.
Haider, N. et al., "Thermolysis of 5-azido-4-arylpyridazin-3(2H)-ones: An efficient and versatile synthesis of pyridazino[4,5-b]indoles", Heterocycles, vol. 68, No. 12, pp. 2549-2561, 2006.
Gong, Y. et al., "Synthesis and biological evaluation of novel pyridazinone-based $\alpha_4$integrin receptor antagonists", Journal of Medicinal Chemistry, vol. 49, No. 11, pp. 3402-3411, 2006.
Lawson, E. C. et al., "Synthesis and biological evaluation of 1,2,4-triazolo[2,3-α]pyrrrole derivatives as alpha-4 ($\alpha_4$) integrin antagonists", Letters in Drug Design and Discovery, vol. 2, No. 8, pp. 601-605, 2005.
Helm, M.D. et al., "A novel approach to functionalised pyridazinone arrays", Organic and Biomolecular Chemistry, vol. 4, pp. 4278-4280, 2006.

(Continued)

Primary Examiner — Susanna Moore
Assistant Examiner — Cecilia M Jaisle
(74) Attorney, Agent, or Firm — Wenderoth, Lind & Ponack, L.L.P.

(57) ABSTRACT

There is provided a compound represented by the formula (I):

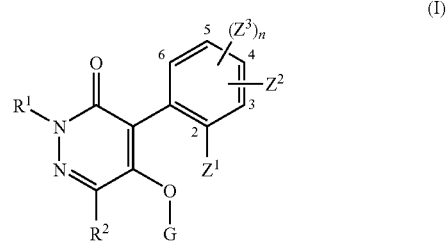

wherein $R^1$ is a $C_{1-6}$ alkyl group or a $(C_{1-6}$ alkyloxy)$C_{1-6}$ alkyl group; $R^2$ is a hydrogen atom or a $C_{1-6}$ alkyl group; G is a hydrogen atom etc.; $Z^1$ is a $C_{1-6}$ alkyl group or a $C_{1-6}$ alkyloxy group; $Z^2$ is a $C_{3-8}$ cycloalkyl group, etc.; $Z^3$ is a $C_{1-6}$ alkyl group, etc.; n is 0, 1, 2 or 3, which has an excellent weed controlling effect.

11 Claims, No Drawings

OTHER PUBLICATIONS

Babichev, F. S. et al., "6-Amino-1-aryl-4-pyridazinones and their derivatives", Ukrainskii Khimicheskii Zhurnal (Russian Edition), vol. 49, No. 11, pp. 1197-1202, 1983. CODEN:UKZHAU ISSN: 0041-6045. Journal Written in Russian. CAN 100:139053, AN 1984:139053, CAPLUS (English language abstract).

Babichev, F. S. et al., "Synthesis of 5-phenyl-6-amino-4-pyridazinones", Dopovidi Akademii Nauk Ukrains'koi RSR, Seriya B: Geologichni, Khimichni ta Biologichni Nauki, vol. 1, pp. 30-33, 1978. CODEN:DANND6, ISSN: 0377-9785. Journal written in Ukrainian. CAN 88:152533, AN 1978:152533, CAPLUS (English language abstract).

English abstract of CN1962642, published May 2007.

International Search Report issued Feb. 23, 2009 in International (PCT) Application No. PCT/JP2008/066918.

Full English Translation of JP 11-152273 published Jun. 8, 1999.

Stevenson, T. M. et al., Application of Cross-Coupling and Metalation Chemistry of 3(2H)-Pyridazinones to Fungicide and Herbicide Discovery, *Journal of Heterocyclic Chemistry*, vol. 42, No. 3 (Apr. 1, 2005), pp. 427-435.

* cited by examiner

PYRIDAZINONE COMPOUND AND HERBICIDE CONTAINING THE SAME

TECHNICAL FIELD

The present invention relates to a pyridazinone compound and a herbicide containing the same.

BACKGROUND ART

The development of compounds that may be used as the active ingredients of herbicides for weed control have been widely advanced, and some compounds having a weed controlling effect have been found.

A certain type of pyridazinone compound is known in J. Heterocycl. Chem., vol. 42, pp. 427-435 (2005).

However, said pyridazinone compound does not have enough weed controlling effect.

DISCLOSURE OF INVENTION

An object of the present invention is to provide a compound having an excellent weed controlling effect.

After extensive investigation, the present inventor found that a pyridazinone compound represented by the following formula (I) has an excellent weed controlling effect. Thus the present invention was completed.

The present invention provides:

(1) a pyridazinone compound represented by the formula (I) (hereinafter, referred to as the compound of the present invention):

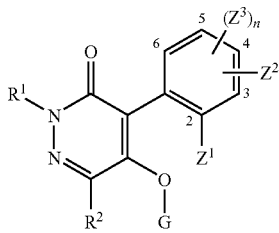

wherein $R^1$ represents a $C_{1-6}$ alkyl group or a $(C_{1-6}$ alkyloxy)$C_{1-6}$ alkyl group;

$R^2$ represents a hydrogen atom or a $C_{1-6}$ alkyl group;

G represents a hydrogen atom or a group represented by any one of the following formulas:

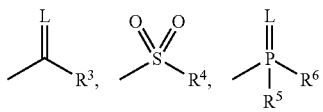

[wherein L represents an oxygen or sulfur atom, $R^3$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a $(C_{6-10}$ aryl)$C_{1-6}$ alkyl group, a $C_{1-6}$ alkyloxy group, a $C_{3-8}$ cycloalkyloxy group, a $C_{2-6}$ alkenyloxy group, a $C_{3-6}$ alkynyloxy group, a $C_{6-10}$ aryloxy group, a $(C_{6-10}$ aryl)$C_{1-6}$ alkyloxy group, a di($C_{1-6}$ alkyl)amino group, a di($C_{2-6}$ alkenyl)amino group, a $(C_{1-6}$ alkyl)($C_{6-10}$ aryl)amino group or a 3- to 8-membered nitrogen-containing heterocyclic group, $R^4$ represents a $C_{1-6}$ alkyl group, a $C_{6-10}$ aryl group or a di($C_{1-6}$ alkyl)amino group, and $R^5$ and $R^6$ may be the same as or different from each other, and represent a $C_{1-6}$ alkyl group, a $C_{3-8}$ cycloalkyl group, a $C_{2-6}$ alkenyl group, a $C_{6-10}$ aryl group, a $C_{1-6}$ alkyloxy group, a $C_{3-8}$ cycloalkyloxy group, a $C_{6-10}$ aryloxy group, a $(C_{6-10}$ aryl)$C_{1-6}$ alkyloxy group, a $C_{1-6}$ alkylthio group or a di($C_{1-6}$ alkyl)amino group, wherein any group $R^4$, $R^5$ and $R^6$ may be substituted with at least one halogen atom, and the $C_{3-8}$ cycloalkyl group, the $C_{6-10}$ aryl group, the aryl moiety of the $(C_{6-10}$ aryl)$C_{1-6}$ alkyl group, the $C_{3-8}$ cycloalkyloxy group, the $C_{6-10}$ aryloxy group, the aryl moiety of the $(C_{6-10}$ aryl)$C_{1-6}$ alkyloxy group, the aryl moiety of the $(C_{1-6}$ alkyl)($C_{6-10}$ aryl)amino group and the 3- to 8-membered nitrogen-containing heterocyclic group may be substituted with at least one $C_{1-6}$ alkyl group];

$Z^1$ represents a $C_{1-6}$ alkyl group or a $C_{1-6}$ alkyloxy group;

$Z^2$ represents a $C_{3-8}$ cycloalkyl group, a $C_{2-6}$ alkynyl group, a $C_{1-6}$ alkyloxy group, a $C_{1-6}$ haloalkyl group, a $C_{1-6}$ haloalkyloxy group, a halogen atom, a $C_{6-10}$ aryl group, a 5- or 6-membered heteroaryl group, a cyano group or a nitro group, and $Z^3$ represents a $C_{1-6}$ alkyl group, a $C_{3-8}$ cycloalkyl group, a $C_{2-6}$ alkynyl group, a $C_{1-6}$ alkyloxy group, a $C_{1-6}$ haloalkyl group, a $C_{1-6}$ haloalkyloxy group, a halogen atom, a $C_{6-10}$ aryl group, a 5- or 6-membered heteroaryl group, a cyano group or a nitro group, wherein the $C_{3-8}$ cycloalkyl group, the $C_{6-10}$ aryl group and the 5- or 6-membered heteroaryl group represented by $Z^2$ and $Z^3$ may be substituted with at least one group selected from the group consisting of a halogen atom and a $C_{1-6}$ alkyl group; and n represents 0, 1, 2 or 3, and when n is 2 or 3, each of $Z^3$ may be the same as or different from each other;

(2) the pyridazinone compound according to the above (1), wherein n is 1, 2 or 3;

(3) the pyridazinone compound according to the above (1) or (2), wherein $Z^2$ is attached to the 4- or 6-position on the benzene ring;

(4) the pyridazinone compound according to any one of the above (1) to (3), wherein n is 1, and $Z^2$ and $Z^3$ are respectively attached to the 4- and 6-positions or the b- and 4-positions on the benzene ring;

(5) the pyridazinone compound according to any one of the above (1) to (4), wherein $Z^1$ represents a $C_{1-3}$ alkyl group, $Z^2$ represents a $C_{3-6}$ cycloalkyl group, a $C_{2-3}$ alkynyl group, a $C_{1-3}$ alkyloxy group, a halogen atom, a cyano group, a nitro group, or a phenyl group which, may be substituted with at least one group selected from the group consisting of a halogen atom and a $C_{1-3}$ alkyl group, and $Z^3$ represents a $C_{1-3}$ alkyl group, a $C_{3-6}$ cycloalkyl group, a $C_{2-3}$ alkynyl group, a $C_{1-3}$ alkyloxy group or a halogen atom;

(6) the pyridazinone compound according to any one of the above (1) to (5), wherein G represents a hydrogen atom or a group represented by any one of the following formulas:

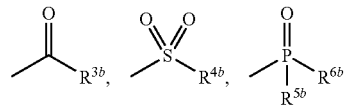

(wherein $R^{3b}$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a $(C_{6-10}$ aryl)$C_{1-6}$ alkyl group, a $C_{1-6}$ alkyloxy group, a $C_{3-8}$ cycloalkyloxy group, a $C_{6-10}$ aryloxy group, a $(C_{6-10}$ aryl)$C_{1-6}$ alkyloxy group or a di($C_{1-6}$ alkyl)amino group, $R^{4b}$ represents a $C_{1-6}$ alkyl group or a $C_{6-10}$ aryl group, and $R^{5b}$ and $R^{6b}$ may be the same as or different from each other, and represent a $C_{1-6}$ alkyl group, a $C_{1-6}$ alkyloxy group, a $C_{6-10}$ aryloxy group or a $C_{1-6}$ alkylthio group, wherein any group represented by $R^{3b}$), $R^{4b}$, $R^{5b}$ and $R^{6b}$ may be substituted with at least one halogen atom, and the $C_{3-8}$ cycloalkyl group, the $C_{6-10}$ aryl group, the aryl moiety of the ($C_{6-10}$ aryl)$C_{1-6}$ alkyl group, the $C_{3-8}$ cycloalkyloxy group, the $C_{6-10}$ aryloxy group, and the aryl moiety of the ($C_{6-10}$ aryl)$C_{1-6}$ alkyloxy group may be substituted with at least one $C_{1-6}$ alkyl group);

(7) the pyridazinone compound according to any one of the above (1) to (5), wherein G represents a hydrogen atom or a group represented by any one of the following formulas:

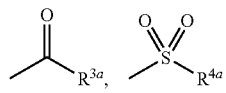

(wherein $R^{3a}$ represents a $C_{1-6}$ alkyl group, a $C_{3-8}$ cycloalkyl group, a $C_{6-10}$ aryl group, a $C_{1-6}$ alkyloxy group or a di($C_{1-6}$ alkyl)amino group, and
$R^{4a}$ represents a $C_{1-6}$ alkyl group, wherein any group represented by $R^{3a}$ and $R^{4a}$ may be substituted with at least one halogen atom, and the $C_{3-8}$ cycloalkyl group and the $C_{6-10}$ aryl group may be substituted with at least one $C_{1-6}$ alkyl group);

(8) the pyridazinone compound according to any one of the above (1) to (7), wherein $R^2$ is a hydrogen atom or a $C_{1-3}$ alkyl group;

(9) the pyridazinone compound according to any one of the above (1) to (7), wherein $R^2$ is a hydrogen atom or a methyl group;

(10) the pyridazinone compound according to any one of the above (1) to (9), wherein $R^1$ is a $C_{1-3}$ alkyl group or a ($C_{1-3}$ alkyloxy)$C_{1-3}$ alkyl group;

(11) a herbicide comprising the pyridazinone compound according to any one of the above (1) to (10) as an active ingredient;

(12) a weed controlling method which comprises applying an effective amount of the pyridazinone compound according to any one of the above (1) to (10) to weeds or soil where weeds are grown;

(13) use of the pyridazinone compound according to any one of the above (1) to (10) for weed control;

(14) a compound represented by the formula (II):

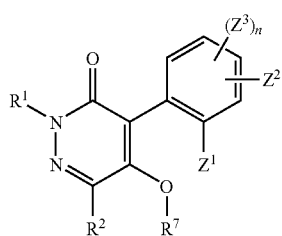

wherein
$R^7$ represents a $C_{1-6}$ alkyl group;
$R^1$ represents a $C_{1-6}$ alkyl group or a ($C_{1-6}$ alkyloxy)$C_{1-6}$ alkyl group;
$R^2$ represents a hydrogen atom or a $C_{1-6}$ alkyl group;
$Z^1$ represents a $C_{1-6}$ alkyl group or a $C_{1-6}$ alkyloxy group;

$Z^2$ represents a $C_{3-8}$ cycloalkyl group, a $C_{2-6}$ alkynyl group, a $C_{1-6}$ alkyloxy group, a $C_{1-6}$ haloalkyl group, a $C_{1-6}$ haloalkyloxy group, a halogen atom, a $C_{6-10}$ aryl group, a 5- or 6-membered heteroaryl group, a cyano group or a nitro group, and $Z^3$ represents a $C_{1-6}$ alkyl group, a $C_{3-8}$ cycloalkyl group, a $C_{2-6}$ alkynyl group, a $C_{1-6}$ alkyloxy group, a $C_{1-6}$ haloalkyl group, a $C_{1-6}$ haloalkyloxy group, a halogen atom, a $C_{6-10}$ aryl group, a 5- or 6-membered heteroaryl group, a cyano group or a nitro group, wherein the $C_{3-8}$ cycloalkyl group, the $C_{6-10}$ aryl group and the 5- or 6-membered heteroaryl group represented by $Z^2$ and $Z^3$ may be substituted with at least one group selected from the group consisting of a halogen atom and a $C_{1-6}$ alkyl group; and n represents 0, 1, 2 or 3, and when n is 2 or 3, each of $Z^3$ may be the same as or different from each other; and

(15) a compound represented by the formula (VI):

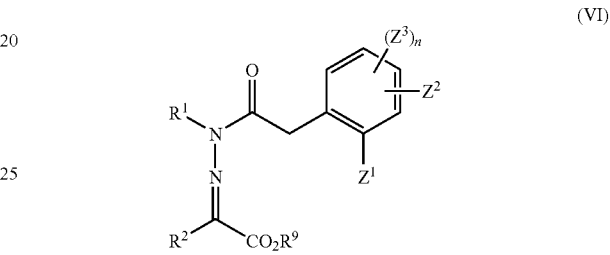

wherein
$R^9$ represents a $C_{1-6}$ alkyl group;
$R^1$ represents a $C_{1-6}$ alkyl group or a ($C_{1-6}$ alkyloxy)$C_{1-6}$ alkyl group;
$R^2$ represents a hydrogen atom or a $C_{1-6}$ alkyl group;
$Z^1$ represents a $C_{1-6}$ alkyl group or a $C_{1-6}$ alkyloxy group;
$Z^2$ represents a $C_{3-8}$ cycloalkyl group, a $C_{2-6}$ alkynyl group, a $C_{1-6}$ alkyloxy group, a $C_{1-6}$ haloalkyl group, a $C_{1-6}$ haloalkyloxy group, a halogen atom, a $C_{6-10}$ aryl group, a 5- or 6-membered heteroaryl group, a cyano group or a nitro group, and $Z^3$ represents a $C_{1-6}$ alkyl group, a $C_{3-8}$ cycloalkyl group, a $C_{2-6}$ alkynyl group, a $C_{1-6}$ alkyloxy group, a $C_{1-6}$ haloalkyl group, a $C_{1-6}$ haloalkyloxy group, a halogen atom, a $C_{6-10}$ aryl group, a 5- or 6-membered heteroaryl group, a cyano group or a nitro group, wherein the $C_{3-8}$ cycloalkyl group, the $C_{6-10}$ aryl group and the 5- or 6-membered heteroaryl group represented by $Z^2$ and $Z^3$ may be substituted with at least one group selected from the group consisting of a halogen atom and a $C_{1-6}$ alkyl group; and n represents 0, 1, 2 or 3, and when n is 2 or 3, each of $Z^3$ may be the same as or different from each other.

The compound of the present invention may be in the form of an agriculturally acceptable salt which is produced by mixing a pyridazinone compound represented by the formula (I) with an inorganic base or the like. The present invention also includes such salts of the pyridazinone compound.

The compound of the present invention has a weed controlling effect.

BEST MODE FOR CARRYING OUT THE INVENTION

The term "$C_{1-6}$ alkyl group", as used herein, means an alkyl group of 1 to 6 carbon atoms, and examples thereof include methyl, ethyl, propyl, isopropyl, butyl, isobutyl, sec-butyl, tert-butyl, pentyl, sec-pentyl, isopentyl, neopentyl, hexyl and isohexyl.

The term "$C_{3-8}$ cycloalkyl group", as used herein, means a cycloalkyl group of 3 to 8 carbon atoms, and examples thereof include cyclopropyl, cyclopentyl and cyclohexyl.

The term "$C_{2-6}$ alkenyl group", as used herein, means an alkenyl group of 2 to 6 carbon atoms, and examples thereof include allyl, 1-buten-3-yl and 3-buten-1-yl.

The term "$C_{2-6}$ alkynyl group", as used herein, means an alkynyl group of 2 to 6 carbon atoms, and examples thereof include propargyl and 2-butynyl.

The term "$C_{6-10}$ aryl group", as used herein, means an aryl group of 6 to 10 carbon atoms, and examples thereof include phenyl and naphthyl.

The term "$(C_{6-10}$ aryl$)C_{1-6}$ alkyl group", as used herein, means a $C_{1-6}$ alkyl group substituted with a $C_{6-10}$ aryl group, and examples thereof include benzyl and phenethyl.

The term "$C_{1-6}$ alkyloxy group", as used herein, means an alkyloxy group of 1 to 6 carbon atoms, and examples thereof include methoxy, ethoxy, propoxy and isopropoxy.

The term "$C_{3-8}$ cycloalkyloxy group", as used herein, means a cycloalkyloxy group of 3 to 8 carbon atoms, and examples thereof include cyclopropyloxy and cyclopentyloxy.

The term "$C_{2-6}$ alkenyloxy group", as used herein, means an alkenyloxy group of 2 to 6 carbon atoms, and examples thereof include vinyloxy and allyloxy.

The term "$C_{3-6}$ alkynyloxy group", as used herein, means an alkynyloxy group of 3 to 6 carbon atoms, and examples thereof include propargyloxy and 2-butynyloxy.

The term "$C_{6-10}$ aryloxy group", as used herein, means an aryloxy group of 6 to 10 carbon atoms, and examples thereof include phenoxy and naphthyloxy.

The term "$(C_{6-10}$ aryl$)C_{1-6}$ alkyloxy group", as used herein, means a $C_{1-6}$ alkyloxy group substituted with a $C_{6-10}$ aryl group, and examples thereof include benzyloxy and phenethyloxy.

The term "di($C_{1-6}$ alkyl)amino group", as used herein, means an amino group substituted with two same or different $C_{1-6}$ alkyl groups, and examples thereof include dimethylamino, diethylamino and N-ethyl-N-methylamino.

The term "di($C_{2-6}$ alkenyl)amino group", as used herein, means an amino group substituted with two same or different $C_{2-6}$ alkenyl groups, and examples thereof include diallylamino and di(3-butenyl)amino.

The term "$(C_{1-6}$ alkyl$)(C_{6-10}$ aryl)amino group", as used herein, means an amino group substituted with a $C_{1-6}$ alkyl group and a $C_{6-10}$ aryl group, and examples thereof include methylphenylamino and ethylphenylamino.

The term "$C_{1-6}$ alkylthio group", as used herein, means an alkylthio group of 1 to 6 carbon atoms, and examples thereof include methylthio, ethylthio, propylthio and isopropylthio.

The term "$(C_{1-6}$ alkyloxy$)C_{1-6}$ alkyl group", as used herein, means a $C_{1-6}$ alkyl group substituted with a $C_{1-6}$ alkyloxy group, and examples thereof include methoxyethyl and ethoxyethyl.

The term "3- to 8-membered nitrogen-containing heterocyclic group", as used herein, means an aromatic or alicyclic 3- to 8-membered heterocyclic group containing 1 to 3 nitrogen atoms and optionally containing 1 to 3 oxygen atoms and/or sulfur atoms, and examples thereof include 1-pyrazolyl, 2-pyridyl, 2-pyrimidinyl, 2-thiazolyl, pyrrolidino, piperidino and morpholino.

The term "5- or 6-membered heteroaryl group", as used herein, means an aromatic 5- or 6-membered heterocyclic group containing 1 to 3 hetero atoms selected from nitrogen, oxygen and sulfur atoms, and examples thereof include 3-pyridyl, 3-thienyl and 1-pyrazolyl.

Examples of the halogen atom, as used herein, include fluorine, chlorine, bromine and iodine atoms.

The "$C_{1-6}$ haloalkyl group" represented by $Z^2$ and $Z^3$ means a $C_{1-6}$ alkyl group substituted with a fluorine atom, chlorine atom, bromine atom, iodine atom or the like, and examples thereof include trifluoromethyl and 2,2,2-trichloroethyl.

The "$C_{1-6}$ haloalkyloxy group" represented by $Z^2$ and $Z^3$ means a $C_{1-6}$ alkyloxy group substituted with a fluorine atom, chlorine atom, bromine atom, iodine atom or the like, and examples thereof include trifluoromethoxy and 2,2,2-trifluoroethoxy.

Among groups represented by $R^3$, $R^4$, $R^5$ and $R^6$, the $C_{3-8}$ cycloalkyl group, the $C_{6-10}$ aryl group, the aryl moiety of the $(C_{6-10}$ aryl$)C_{1-6}$ alkyl group, the $C_{3-8}$ cycloalkyloxy group, the $C_{6-10}$ aryloxy group, the aryl moiety of the $(C_{6-10}$ aryl$)C_{1-6}$ alkyloxy group, the aryl moiety of the $(C_{1-6}$ alkyl$)(C_{6-10}$ aryl)amino group and the 3- to 8-membered nitrogen-containing heterocyclic group may be substituted with at least one $C_{1-6}$ alkyl group. Examples of the $C_{1-6}$ alkyl group as such a substituent include methyl, ethyl, propyl and butyl.

Among groups represented by $Z^2$ and $Z^3$, the $C_{3-8}$ cycloalkyl group, the $C_{6-10}$ aryl group and the 5- or 6-membered heteroaryl group may be substituted with at least one $C_{1-6}$ alkyl group. Examples of the $C_{1-6}$ alkyl group as such a substituent include methyl, ethyl, propyl and butyl.

A compound represented by the formula (I-a), which is the compound of the present invention wherein G is a hydrogen atom, may exist in a form of tautomers represented by the formulas (I-a') and (I-a"). The compound represented by the formula (I-a) includes all of such tautomers and a mixture of two or more of them.

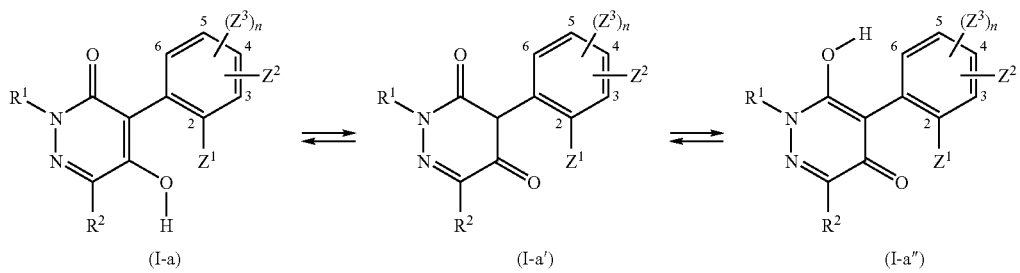

The compound represented by the formula (I-a) may be in the form of an agriculturally acceptable salt which is produced by being mixed with an inorganic base (for example, hydroxide, carbonate, hydrogen carbonate, acetate, or hydride of an alkali metal (lithium, sodium, potassium, etc.); hydroxide or hydride of an alkali earth metal (magnesium, calcium, barium, etc.); ammonia), an organic base (for example, dimethylamine, triethylamine, piperazine, pyrrolidine, piperidine, 2-phenylethylamine, benzylamine, ethanolamine, diethanolamine, pyridine, or collidine) or a metal alkoxide (for example, sodium methoxide, potassium tert-butoxide, or magnesium methoxide). The compound represented by the formula (I-a) includes such agriculturally acceptable salts of the pyridazinone compound.

When the compound of the present invention has one or more asymmetric centers, there are two or more stereoisomers (e.g., enantiomer and diastereomer) of the compound of the present invention. The compound of the present invention includes all of such stereoisomers and a mixture of two or more of them.

When the compound of the present invention has geometric isomerism based on a double bond or the like, there are two or more geometric isomers (e.g., E/Z or trans/cis isomers, and S-trans/S-cis isomers) of the compound of the present invention. The compound of the present invention includes all of such geometric isomers and a mixture of two or more of them.

Preferred examples of the compound of the present invention include the following compounds.

A pyridazinone compound represented by the formula (I), wherein n is 1, 2 or 3.

A pyridazinone compound represented by the formula (I), wherein $Z^2$ is attached to the 4- or 6-position on the benzene ring.

A pyridazinone compound represented by the formula (I), wherein n is 1, and $Z^2$ and $Z^3$ are respectively attached to the 4- and 6-positions or the 6- and 4-positions on the benzene ring.

A pyridazinone compound represented by the formula (I), wherein G is a hydrogen atom or a group represented by any one of the following formulas:

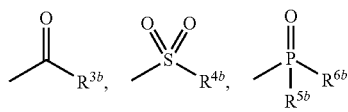

(wherein $R^{3b}$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a $(C_{6-10}$ aryl)$C_{1-6}$ alkyl group, a $C_{1-6}$ alkyloxy group, a $C_{3-8}$ cycloalkyloxy group, a $C_{6-10}$ aryloxy group, a $(C_{6-10}$ aryl)$C_{1-6}$ alkyloxy group or a di($C_{1-6}$ alkyl)amino group; $R^{4b}$ represents a $C_{1-6}$ alkyl group or a $C_{6-10}$ aryl group; and $R^{5b}$ and $R^{6b}$ may be the same as or different from each other, and represent a $C_{1-6}$ alkyl group, a $C_{1-6}$ alkyloxy group, a $C_{6-10}$ aryloxy group or a $C_{1-6}$ alkylthio group, wherein any group represented by $R^{3b}$, $R^{4b}$, $R^{5b}$ and $R^{6b}$ may be substituted with at least one halogen atom, and the $C_{3-8}$ cycloalkyl group, the $C_{6-10}$ aryl group, the aryl moiety of the $(C_{6-40}$ aryl)$C_{1-6}$ alkyl group, the $C_{3-8}$ cycloalkyloxy group, the $C_{6-10}$ aryloxy group and the aryl moiety of the $(C_{6-10}$ aryl)$C_{1-6}$ alkyloxy group may be substituted with at least one $C_{1-6}$ alkyl group).

A pyridazinone compound represented by the formula (I), wherein G is a hydrogen atom or a group represented by any one of the following formulas:

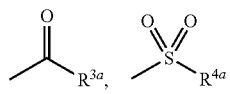

(wherein $R^{3a}$ represents a $C_{1-6}$ alkyl group, a $C_{3-8}$ cycloalkyl group, a $C_{6-10}$ aryl group, a $C_{1-6}$ alkyloxy group or a di($C_{1-6}$ alkyl)amino group; and $R^{4a}$ represents a $C_{1-6}$ alkyl group, wherein any group represented by $R^{3a}$ and $R^{4a}$ may be substituted with at least one halogen atom, and the $C_{3-8}$ cycloalkyl group and the $C_{6-10}$ aryl group may be substituted with at least one $C_{1-6}$ alkyl group).

A pyridazinone compound represented by the formula (I), wherein $R^1$ is a $C_{1-3}$ alkyl group or a $(C_{1-3}$ alkyloxy)$C_{1-3}$ alkyl group.

A pyridazinone compound represented by the formula (I), wherein $R^2$ is a hydrogen atom or a $C_{1-3}$ alkyl group.

A pyridazinone compound represented by the formula (I), wherein $R^2$ is a hydrogen atom or a methyl group.

A pyridazinone compound represented by the formula (I), wherein $Z^1$ is a $C_{1-3}$ alkyl group, $Z^2$ is a $C_{3-6}$ cycloalkyl group, a $C_{2-3}$ alkynyl group, a $C_{1-3}$ alkyloxy group, a $C_{1-3}$ haloalkyl group, a $C_{1-3}$ haloalkyloxy group, a halogen atom, a cyano group or a nitro group, or a phenyl group which may be substituted with at least one group selected from the group consisting of a halogen atom and a $C_{1-3}$ alkyl group, and $Z^3$ is a $C_{1-3}$ alkyl group, a $C_3$-$L_6$ cycloalkyl group, a $C_{2-3}$ alkynyl group, a $C_{1-3}$ alkyloxy group or a halogen atom.

A pyridazinone compound represented by the formula (I), wherein $R^1$ is a $C_{1-3}$ alkyl group or a $(C_{1-3}$ alkyloxy)$C_{1-3}$ alkyl group, and $R^2$ is a hydrogen atom or a $C_{1-3}$ alkyl group.

A pyridazinone compound represented by the formula (I), wherein $R^1$ is a $C_{1-3}$ alkyl group or a $(C_{1-3}$ alkyloxy)$C_{1-3}$ alkyl group, and $R^2$ is a hydrogen atom or a methyl group.

A pyridazinone compound represented by the formula (I), wherein $R^2$ is a hydrogen atom or a $C_{1-3}$ alkyl group, and G is a hydrogen atom or a group represented by any one of the following formulas:

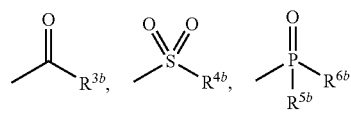

(wherein $R^{3b}$, $R^{4b}$, $R^{5b}$ and $R^{6b}$ are as defined above).

A pyridazinone compound represented by the formula (I), wherein $R^2$ is a hydrogen atom or a $C_{1-3}$ alkyl group, and G is a hydrogen atom or a group represented by any one of the following formulas:

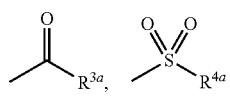

(wherein $R^{3a}$ and $R^{4a}$ are as defined above).

A pyridazinone compound represented by the formula (I), wherein $R^2$ is a hydrogen atom or a methyl group, and G is a hydrogen atom or a group represented by any one of the following formulas:

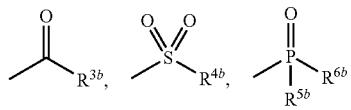

(wherein $R^{3b}$, $R^{4b}$, $R^{5b}$ and $R^{6b}$ are as defined above).

A pyridazinone compound represented by the formula (I), wherein $R^2$ is a hydrogen atom or a methyl group, and G is a hydrogen atom or a group represented by any one of the following formulas:

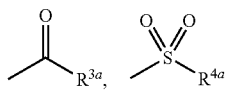

(wherein $R^{3a}$ and $R^{4a}$ are as defined above).

A pyridazinone compound represented by the formula (I), wherein $R^1$ is a $C_{1-3}$ alkyl group or a $(C_{1-3}$ alkyloxy$)C_{1-3}$ alkyl group, $R^2$ is a hydrogen atom or a $C_{1-3}$ alkyl group, and G is a hydrogen atom or a group represented by any one of the following formulas:

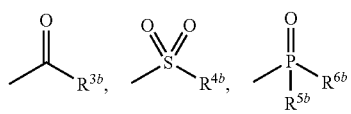

(wherein $R^{3b}$, $R^{4b}$, $R^{5b}$ and $R^{6b}$ are as defined above).

A pyridazinone compound represented by the formula (I), wherein $R^1$ is a $C_{1-3}$ alkyl group or a $(C_{1-3}$ alkyloxy$)C_{1-3}$ alkyl group, $R^2$ is a hydrogen atom or a $C_{1-3}$ alkyl group, and G is a hydrogen atom or a group represented by any one of the following formulas:

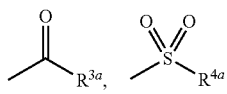

(wherein $R^{3a}$ and $R^{4a}$ are as defined above).

A pyridazinone compound represented by the formula (I), wherein $R^1$ is a $C_{1-3}$ alkyl group or a $(C_{1-3}$ alkyloxy$)C_{1-3}$ alkyl group, $R^2$ is a hydrogen atom or a methyl group, and G is a hydrogen atom or a group represented by any one of the following formulas:

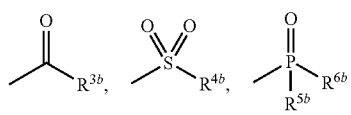

(wherein $R^{3b}$, $R^{4b}$, $R^{5b}$ and $R^{6b}$ are as defined above).

A pyridazinone compound represented by the formula (I), wherein $R^2$ is a hydrogen atom or a methyl group, and G is a hydrogen atom or a group represented by any one of the following formulas:

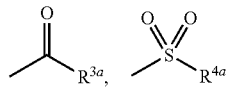

(wherein $R^{3a}$ and $R^{4a}$ are as defined above).

A pyridazinone compound represented by the formula (I), wherein $R^1$ is a $C_{1-3}$ alkyl group or a $(C_{1-3}$ alkyloxy$)C_{1-3}$ alkyl group, $R^2$ is a hydrogen atom or a $C_{1-3}$ alkyl group,
n is 1, $Z^2$ and $Z^3$ are respectively attached to the 4- and 6-positions or the 6- and 4-positions on the benzene ring,
$Z^1$ is a $C_{1-6}$ alkyl group (more preferably a $C_{1-3}$ alkyl group),
$Z^2$ is a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group), a $C_{1-6}$ haloalkyl group (more preferably a $C_{1-3}$ haloalkyl group), a $C_{1-6}$ haloalkyloxy group (more preferably a $C_{1-3}$ haloalkyloxy group), a halogen atom, a cyano group, a nitro group, or a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group), and
$Z^3$ is a $C_{1-6}$ alkyl group (more preferably a $C_{1-3}$ alkyl group), a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group) or a halogen atom.

A pyridazinone compound represented by the formula (I), wherein $R^1$ is a $C_{1-3}$ alkyl group or a $(C_{1-3}$ alkyloxy$)C_{1-3}$ alkyl group, $R^2$ is a hydrogen atom or a $C_{1-3}$ alkyl group, G is a hydrogen atom or a group represented by any one of the following formulas:

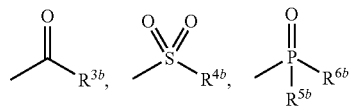

(wherein $R^{3b}$, $R^{4b}$, $R^{5b}$ and $R^{6b}$ are as defined above),
n is 1, $Z^2$ and $Z^3$ are respectively attached to the 4- and 6-positions or the 6- and 4-positions on the benzene ring,
$Z^1$ is a $C_{1-6}$ alkyl group (more preferably a $C_{1-3}$ alkyl group),
$Z^2$ is a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group), a $C_{1-6}$ haloalkyl group (more preferably a $C_{1-3}$ haloalkyl group), a $C_{1-6}$ haloalkyloxy group (more preferably a $C_{1-3}$ haloalkyloxy group), a halogen atom, a cyano group, a nitro group, or a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group), and
$Z^3$ is a $C_{1-6}$ alkyl group (more preferably a $C_{1-3}$ alkyl group), a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group) or a halogen atom.

A pyridazinone compound represented by the formula (I), wherein $R^1$ is a $C_{1-3}$ alkyl group or a $(C_{1-3}$ alkyloxy$)C_{1-3}$ alkyl group, $R^2$ is a hydrogen atom or a $C_{1-3}$ alkyl group, G is a hydrogen atom or a group represented by any one of the following formulas:

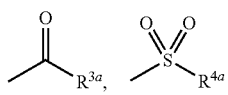

(wherein $R^{3a}$ and $R^{4a}$ are as defined above), n is 1, $Z^2$ and $Z^3$ are respectively attached to the 4- and 6-positions or the 6- and 4-positions on the benzene ring, $Z^1$ is a $C_{1-6}$ alkyl group (more preferably a $C_{1-3}$ alkyl group), $Z^2$ is a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group), a $C_{1-6}$ haloalkyl group (more preferably a $C_{1-3}$ haloalkyl group), a $C_{1-6}$ haloalkyloxy group (more preferably a $C_{1-3}$ haloalkyloxy group), a halogen atom, a cyano group, a nitro group, or a $C_{6-10}$ aryl group (more preferably phenyl group) which may be substituted with at least one group selected from the group consisting of a halogen atom and a $C_{1-6}$ alkyl group (more preferably a $C_{1-3}$ alkyl group), and $Z^3$ is a $C_{1-6}$ alkyl group (more preferably a $C_{1-3}$ alkyl group), a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group) or a halogen atom.

A pyridazinone compound represented by the formula (I), wherein $R^1$ is a $C_{1-3}$ alkyl group or a ($C_{1-3}$ alkyloxy)$C_{1-3}$ alkyl group, $R^2$ is a hydrogen atom or a methyl group, n is 1, $Z^2$ and $Z^3$ are respectively attached to the 4- and 6-positions or the 6- and 4-positions on the benzene ring, $Z^1$ is a $C_{1-6}$ alkyl group (more preferably a $C_{1-3}$ alkyl group), $Z^2$ is a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group), a $C_{1-6}$ haloalkyl group (more preferably a $C_{1-3}$ haloalkyl group), a $C_{1-6}$ haloalkyloxy group (more preferably a $C_{1-3}$ haloalkyloxy group), a halogen atom, a cyano group, a nitro group, or a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group), and $Z^3$ is a $C_{1-6}$ alkyl group (more preferably a $C_{1-3}$ alkyl group), a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group) or a halogen atom.

A pyridazinone compound represented by the formula (I), wherein $R^1$ is a $C_{1-3}$ alkyl group or a ($C_{1-3}$ alkyloxy)$C_{1-3}$ alkyl group, $R^2$ is a hydrogen atom or a methyl group, G is a hydrogen atom or a group represented by any one of the following formulas:

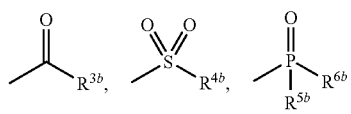

(wherein $R^{3b}$, $R^{4b}$, $R^{5b}$ and $R^{6b}$ are as defined above), n is 1, $Z^2$ and $Z^3$ are respectively attached to the 4- and 6-positions or the 6- and 4-positions on the benzene ring, $Z^1$ is a $C_{1-6}$ alkyl group (more preferably a $C_{1-3}$ alkyl group), $Z^2$ is a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group), a $C_{1-6}$ haloalkyl group (more preferably a $C_{1-3}$ haloalkyl group), a $C_{1-6}$ haloalkyloxy group (more preferably a $C_{1-3}$ haloalkyloxy group), a halogen atom, a cyano group, a nitro group, or a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group), and $Z^3$ is a $C_{1-6}$ alkyl group (more preferably a $C_{1-3}$ alkyl group), a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group) or a halogen atom.

A pyridazinone compound represented by the formula (I), wherein $R^1$ is a $C_{1-3}$ alkyl group or a ($C_{1-3}$ alkyloxy)$C_{1-3}$ alkyl group, $R^2$ is a hydrogen atom or a methyl group, G is a hydrogen atom or a group represented by any one of the following formulas:

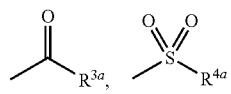

(wherein $R^{3a}$ and $R^{4a}$ are as defined above), n is 1, $Z^2$ and $Z^3$ are respectively attached to the 4- and 6-positions or the 6- and 4-positions on the benzene ring, $Z^1$ is a $C_{1-6}$ alkyl group (more preferably a $C_{1-3}$ alkyl group), $Z^2$ is a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group), a $C_{1-6}$ haloalkyl group (more preferably a $C_{1-3}$ haloalkyl group), a $C_{1-6}$ haloalkyloxy group (more preferably a $C_{1-3}$ haloalkyloxy group), a halogen atom, a cyano group, a nitro group, or a $C_{6-10}$ aryl group (more preferably a phenyl group) which may be substituted with at least one group selected from the group consisting of a halogen atom and a $C_{1-6}$ alkyl group (More preferably a $C_{1-3}$ alkyl group), and $Z^3$ is a $C_{1-6}$ alkyl group (more preferably a $C_{1-3}$ alkyl group), a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group) or a halogen atom.

A pyridazinone compound represented by the formula (I), wherein n is 0 and $Z^2$ is attached to the 5-position on the benzene ring.

A pyridazinone compound represented by the formula (I), wherein $R^1$ is a $C_{1-3}$ alkyl group or a ($C_{1-3}$ alkyloxy)$C_{1-3}$ alkyl group, $R^2$ is a hydrogen atom or a $C_{1-3}$ alkyl group, n is 0, $Z^2$ is attached to the 5-position on the benzene ring, $Z^1$ is a $C_{1-6}$ alkyl group (more preferably a $C_{1-3}$ alkyl group), and $Z^2$ is a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group).

A pyridazinone compound represented by the formula (I), wherein $R^1$ is a $C_{1-3}$ alkyl group or a ($C_{1-3}$ alkyloxy)$C_{1-3}$ alkyl group, $R^2$ is a hydrogen atom or a $C_{1-3}$ alkyl group, G is a hydrogen atom or a group represented by any one of the following formulas:

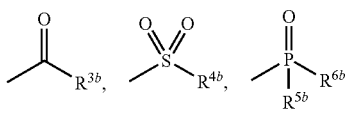

(wherein $R^{3b}$, $R^{4b}$, $R^{5b}$ and $R^{6b}$ are as defined above),
n is 0, $Z^2$ is attached to the 5-position on the benzene ring,
$Z^1$ is a $C_{1-6}$ alkyl group (more preferably a $C_{1-3}$ alkyl group), and
$Z^2$ is a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group).

A pyridazinone compound represented by the formula (I), wherein $R^1$ is a $C_{1-3}$ alkyl group or a $(C_{1-3}$ alkyloxy$)C_{1-3}$ alkyl group, $R^2$ is a hydrogen atom or a $C_{1-3}$ alkyl group, G is a hydrogen atom or a group represented by any one of the following formulas:

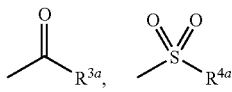

(wherein $R^{3a}$ and $R^{4a}$ are as defined above),
n is 0, $Z^2$ is attached to the 5-position on the benzene ring,
$Z^1$ is a $C_{1-6}$ alkyl group (more preferably a $C_{1-3}$ alkyl group), and
$Z^2$ is a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group).

A pyridazinone compound represented by the formula (I), wherein $R^1$ is a $C_{1-3}$ alkyl group or a $(C_{1-3}$ alkyloxy$)C_{1-3}$ alkyl group, $R^2$ is a hydrogen atom or a methyl group,
n is 0, $Z^2$ is attached to the 5-position on the benzene ring,
$Z^1$ is a $C_{1-6}$ alkyl group (more preferably a $C_{1-3}$ alkyl group), and
$Z^2$ is a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group).

A pyridazinone compound represented by the formula (I), wherein $R^1$ is a $C_{1-3}$ alkyl group or a $(C_{1-3}$ alkyloxy$)C_{1-3}$ alkyl group, $R^2$ is a hydrogen atom or a methyl group, G is a hydrogen atom or a group represented by any one of the following formulas:

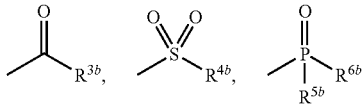

(wherein $R^{3b}$, $R^{4b}$, $R^{5b}$ and $R^{6b}$ are as defined above),
n is 0, is attached to the 5-position on the benzene ring,
$Z^1$ is a $C_{1-6}$ alkyl group (more preferably a $C_{1-3}$ alkyl group), and
$Z^2$ is a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group).

A pyridazinone compound represented by the formula (I), wherein $R^1$ is a $C_{1-3}$ alkyl group or a $(C_{1-3}$ alkyloxy$)C_{1-3}$ alkyl group, $R^2$ is a hydrogen atom or a methyl group, G is a hydrogen atom or a group represented by any one of the following formulas:

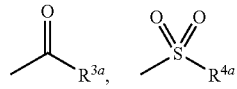

(wherein $R^{3a}$ and $R^{4a}$ are as defined above),
n is 0, $Z^2$ is attached to the 5-position on the benzene ring,
$Z^1$ is a $C_{1-6}$ alkyl group (more preferably a $C_{1-3}$ alkyl group), and
$Z^2$ is a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group).

Preferred examples of the compound of the present invention further include pyridazinone compounds represented by the following formulas (I-1), (I-2) and (I-3).

The formula (I-1):

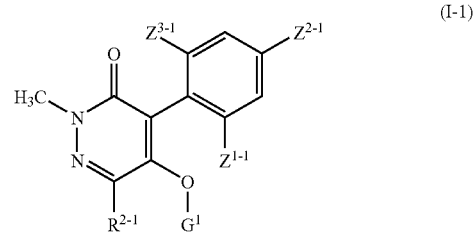

(I-1)

wherein $R^{2-1}$ represents a hydrogen atom or a $C_{1-3}$ alkyl group, $G^1$ represents a hydrogen atom, a $C_{1-3}$ alkylcarbonyl group which may be substituted with at least one halogen atom, a $C_{1-3}$ alkoxycarbonyl group or a $C_{6-10}$ arylcarbonyl group, $Z^{1-1}$ represents a $C_{1-3}$ alkyl group, $Z^{2-1}$ represents a $C_{3-6}$ cycloalkyl group, a $C_{2-3}$ alkynyl group, a $C_{1-3}$ alkyloxy group, a $C_{1-3}$ haloalkyl group, a $C_{1-3}$ haloalkyloxy group, a halogen atom, a cyano group, a nitro group, or a phenyl group which may be substituted with at least one group selected from the group consisting of a halogen atom and a $C_{1-3}$ alkyl group, and $Z^{3-1}$ represents a hydrogen atom, a $C_{1-3}$ alkyl group, a $C_{3-6}$ cycloalkyl group, a $C_{2-3}$ alkynyl group, a $C_{1-3}$ alkyloxy group or a halogen atom.

In the formula (I-1), $R^{2-1}$ is preferably a hydrogen atom, a methyl group or an ethyl group, $G^1$ is preferably a hydrogen atom, an acetyl group, a propionyl group, a methoxycarbonyl group, an ethoxycarbonyl group or a benzoyl group, $Z^{1-1}$ is preferably a methyl group or an ethyl group, $Z^{2-1}$ is preferably a cyclopropyl group, an ethynyl group, a methoxy group, a trifluoromethyl group, a trifluoromethoxy group, a chlorine atom, a bromine atom, a phenyl group, a 4-methylphenyl group, a cyano group or a nitro group, and $Z^{3-1}$ is preferably a hydrogen atom, a methyl group, an ethyl group, a cyclopropyl group, an ethynyl group, a methoxy group, a chlorine atom or a bromine atom.

The formula (I-2):

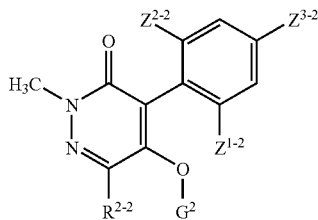

(I-2)

wherein $R^{2-2}$ represents a hydrogen atom or a $C_{1-3}$ alkyl group, $G^2$ represents a hydrogen atom, a $C_{1-3}$ alkylcarbonyl group which may be substituted with at least one halogen atom, a $C_{1-3}$ alkoxycarbonyl group or a $C_{6-10}$ arylcarbonyl group, $Z^{1-2}$ represents a $C_{1-3}$ alkyl group, $Z^{2-2}$ represents a $C_{3-6}$ cycloalkyl group, a $C_{2-3}$ alkynyl group, a $C_{1-3}$ alkyloxy group, a halogen atom, a cyano group or a nitro group, and $Z^{3-2}$ represents a hydrogen atom, a $C_{1-3}$ alkyl group, a $C_{3-6}$ cycloalkyl group, a $C_{2-3}$ alkynyl group, a $C_{1-3}$ alkyloxy group or a halogen atom.

In the formula (I-2), $R^{2-2}$ is preferably a hydrogen atom, a methyl group or an ethyl group, $G^2$ is preferably a hydrogen atom, an acetyl group, a propionyl group, a methoxycarbonyl group, an ethoxycarbonyl group or a benzoyl group, $Z^{1-2}$ is preferably a methyl group or an ethyl group, $Z^{2-2}$ is preferably a cyclopropyl group, an ethynyl group, a methoxy group, a chlorine atom, a bromine atom, a cyano group or nitro group, and $Z^{3-2}$ is preferably a hydrogen atom, a methyl group, an ethyl group, a cyclopropyl group, an ethynyl group, a methoxy group, a chlorine atom or a bromine atom.

The formula (I-3):

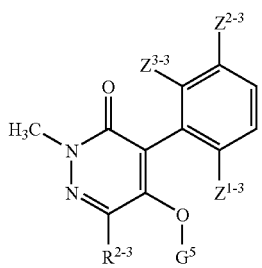

(I-3)

wherein $R^{2-3}$ represents a hydrogen atom or a $C_{1-3}$ alkyl group, $G^5$ represents a hydrogen atom, a $C_{1-3}$ alkylcarbonyl group which may be substituted with at least one halogen atom, a alkoxycarbonyl group or a $C_{6-10}$ arylcarbonyl group, $Z^{1-3}$ represents a $C_{1-3}$ alkyl group, $Z^{2-3}$ represents a phenyl group which may be substituted with at least one group selected from the group consisting of a halogen atom and a $C_{1-3}$ alkyl group, and $Z^{3-3}$ represents a hydrogen atom, a $C_{1-3}$ alkyl group or a halogen atom.

In the formula (I-3), $R^{2-3}$ is preferably a hydrogen atom, a methyl group or an ethyl group, $G^5$ is preferably a hydrogen atom, an acetyl group, a propionyl group, a methoxycarbonyl group, an ethoxycarbonyl group or a benzoyl group, $Z^{1-3}$ is preferably a methyl group or an ethyl group, $Z^{2-3}$ is preferably a phenyl group, a 4-fluorophenyl group or a 4-chlorophenyl group, and $Z^{3-3}$ is preferably a hydrogen atom, a methyl group or a chlorine atom.

The compound of the present invention has an excellent weed controlling effect, and can be used as an active ingredient of a herbicide. Some of the compounds of the present invention have excellent selectivity between crop plants and weeds.

Another aspect of the present invention is a herbicide comprising the compound of the present invention as an active ingredient.

Examples of weeds which the compound of the present invention can control include:

weeds growing in fields such as *Digitaria adscendens, Eleusine indica, Setaria viridis, Setaria faberi, Setaria glauca, Echinochloa crus-galli, Panicum dichotomiflorum, Panicum texanum, Brachiaria platyphylla, Sorghum halepense, Sorghum bicolor, Cynodon dactylon, Avena fatua, Lolium multiflorum, Alopecurus myosuroides, Bromus tectorum, Bromus sterilis, Phalaris minor, Apera spica-venti, Poa annua, Agropyron repens, Cyperus iria, Cyperus rotundus, Cyperus esculentus, Portulaca oleracea, Amaranthus retroflexus, Amaranthus hybridus, Abutilon theophrasti, Sida spinosa, Polygonum convolvulus, Polygonum lapathifolium, Polygonum pennsylvanicum, Polygonum persicaria, Rumex crispus, Rumex obtusifolius, Polygonum cuspidatum, Chenopodium album, Kochia scoparia, Polygonum longisetum, Solanum nigrum, Datura stramonium, Ipomoea purpurea, Ipomoea hederacea, Ipomoea hederacea* var. *integriuscula, Ipomoea lacunosa, Convolvulus arvensis, Lamium purpureum, Lamium amplexicaule, Xanthium strumarium, Helianthus* spp. (wild sunflower), *Matricaria inodora, Matricaria chamomilla, Chrysanthemum segetum, Matricaria matricarioides, Ambrosia artemisiifolia, Ambrosia trifida, Erigeron Canadensis, Artemisia princeps, Solidago altissima, Sesbania exaltata, Cassia obtusifolia, Desmodium tortuosum, Trifolium repens, Pueraria lobata, Vicia sativa, Commelina communis, Commelina benghalensis, Galium aparine, Stellaria media, Raphanus raphanistrum, Sinapis arvensis, Capsella bursa-pastoris, Veronica persica, Veronica hederifolia, Viola arvensis, Viola tricolor, Papaver rhoeas, Myosotis scorpioides, Asclepias syriaca, Euphorbia helioscopia, Euphorbia maculata, Geranium carolinianum, Erodium cicutarium, Equisetum arvense*, and the like; and weeds in paddy fields such as *Echinochloa oryzicola, Echinochloa crus-galli, Cyperus difformis, Cyperus iria, Fimbristylis miliacea, Eleocharis acicularis, Scirpus juncoides, Scirpus wallichii, Cyperus serotinus, Eleocharis kuroguwai, Scirpus maritimus, Scirpus nipponicus, Monochoria vaginalis, Lindernia procumbens, Dopatrium junceum, Rotala indica, Ammannia multiflora, Elatine triandra, Ludwigia prostrata, Sagittaria pygmaea, Alisma canaliculatum, Sagittaria trifolia, Potamogeton distinctus, Oenanthe javanica, Callitriche verna, Vandellia angustifolia, Lindernia dubia, Eclipta prostrata, Murdannia keisak, Paspalum distichum, Leersia oryzoides*, and the like.

The herbicide of the present invention is generally prepared by dissolving or dispersing the compound of the present invention in a suitable liquid carrier, or mixing the compound of the present invention with a suitable solid carrier, or adsorbing the compound of the present invention onto a suitable solid carrier, and then formulating into a dosage form suitable for the intended use. The herbicide of the present invention takes, for example, the form of an emulsifiable concentrate, a soluble concentrate, an oil solution, an aerosol, a wettable powder, a dust, a less drifting dust, a granule, a micro granule, a micro granule F, a fine granule F, a water dispersible granule, a water soluble powder, a flowable, a dry flowable, a jumbo tablet, a tablet, a paste or the like. The herbicide of the present invention may further contain an auxiliary agent such as an emulsifier, a dispersant, a spreading agent, a penetrating agent, a wetting agent, a binder, a thickener, a preservative, an antioxidant, a colorant or the like, as needed. Such formulation of the herbicide of the present invention can be produced according to a known method.

Examples of the liquid carrier include water, alcohols (such as methanol, ethanol, 1-propanol, 2-propanol, or ethylene glycol), ketones (such as acetone, or methyl ethyl ketone), ethers (such as dioxane, tetrahydrofuran, ethylene glycol monomethyl ether, diethylene glycol monomethyl ether, or propylene glycol monomethyl ether), aliphatic hydrocarbons (such as hexane, octane, cyclohexane, kerosene, fuel oil, or machine oil), aromatic hydrocarbons (such as benzene, toluene, xylene, solvent naphtha, or methylnaphthalene), halogenated hydrocarbons (such as dichloromethane, chloroform, or carbon tetrachloride), acid amides (such as dimethylformamide, dimethylacetamide, or N-methylpyrrolidone), esters (such as ethyl acetate, butyl acetate, or glyceryl fatty acid ester), nitriles (such as acetonitrile, or propionitrile), and the like. Two or more of such liquid carriers may be used as a mixture in a proper ratio.

Examples of the solid carrier include vegetable powder (for example, soybean powder, tobacco powder, wheat flour, or wood flour), mineral powders (for example, clays such as kaolin, bentonite, acidic white clay and clay, talcs such as talcum powder and pyrophyllite powder, silicas such as diatomaceous earth and mica powder,), alumina, sulfur powder, activated charcoal, saccharides (for example, lactose, or glucose), inorganic salts (for example, calcium carbonate, or sodium hydrogen carbonate), glass hollow bodies (natural vitreous materials being calcined to encapsulate air bubbles in them) and the like. Two or more of such solid carriers may be used as a mixture in a proper ratio.

The herbicide of the present invention comprises generally 1 to 99% by weight, preferably about 10 to 99% by weight of the liquid carrier or solid carrier.

A surfactant is generally used as an emulsifier, a dispersant, a spreading agent, a penetrating agent or a wetting agent. Examples of the surfactant include anionic surfactants such as alkyl sulfate ester salts, alkylarylsulfonates, dialkyl sulfosuccinates, polyoxyethylene alkylaryl ether phosphate salts, lignin sulfonates, naphthalenesulfonate-formaldehyde polycondensates and the like, and nonionic surfactants such as polyoxyethylene alkyl ethers, polyoxyethylene alkylaryl ethers, polyoxyethylenealkyl polyoxypropylene block copolymers, sorbitan fatty acid esters and the like. Two or more of such surfactants may be used. The herbicide of the present invention comprises generally 0.1 to 50% by weight, preferably about 0.1 to 25% by weight of the surfactant.

Examples of the binder and the thickener include dextrin, sodium salt of carboxylmethylcellulose, polycarboxylic acid type polymers, polyvinylpyrrolidone, polyvinyl alcohol, sodium lignin sulfonate, calcium lignin sulfonate, sodium polyacrylate, gum acacia, sodium alginate, mannitol, sorbitol, bentonite type mineral matters, polyacrylic acid and derivatives thereof, white carbon, natural saccharide derivatives (for example, xanthan gum, guar gum, and the like) and the like.

The content of the compound of the present invention in the herbicide of the present invention is generally 1 to 90% by weight in the form of the emulsifiable concentrate, wettable powder, water dispersible granule, soluble concentrate, water soluble powder, flowable and the like, generally 0.01 to 10% by weight in the form of the oil solution, dust, less drifting dust and the like, and generally 0.05 to 10% by weight in the form of the micro granule, micro granule F, fine granule F, granule and the like. The content of the compound of the present invention in the herbicide of the present invention may be appropriately varied depending on the intended use. The emulsifiable concentrate, wettable powder, water dispersible granule, soluble concentrate, water soluble powder, flowable and the like are generally diluted with water or the like appropriately and then used, and they are generally used after about 100 to 100,000-fold dilution.

Another aspect of the present invention is a weed controlling method which comprises applying an effective amount of the compound of the present invention to weeds or soil where weeds grow.

For the weed controlling method of the present invention, the herbicide of the present invention may be used as the compound of the present invention.

The herbicide of the present invention can be applied by a similar method to a known application method for conventional agricultural chemicals, including aerial spraying, soil broadcast, foliage application and the like.

When the herbicide of the present invention is used in dry or paddy fields, the amount used (i.e.; effective amount) of the herbicide of the present invention may differ according to on an applied area, an applied time of year, an application method, target weed species, cultivated crop and the like, and it is generally in the range of about 1 to 5000 g, preferably about 10 to 1000 g of the compound of the present invention per hectare of dry or paddy field.

When the herbicide of the present invention is used for weed control in dry fields, it is generally used as a pre-emergence soil incorporation treatment agent, a pre-emergence soil treatment agent or a post-emergence foliage treatment agent. When the herbicide of the present invention is used for weed control in paddy fields, it is generally used as a flooded soil treatment agent or an agent for both foliage and soil treatment.

The herbicide of the present invention can be applied simultaneously with one or more kinds of other herbicides, plant growth regulators, fungicides, insecticides, acaricides, nematocides and the like, if necessary. The herbicide of the present invention may also contain the active ingredients of one or more kinds of other herbicides, plant growth regulators, fungicides, insecticides, acaricides, nematocides and the like. The herbicide of the present invention may be also used in combination with the active ingredients of one or more kinds of other herbicides, plant growth regulators, fungicides, insecticides, acaricides, nematocides and the like.

Examples of the active ingredients of such other herbicides include:

(1) herbicidal phenoxyfatty acid compounds [2,4-PA, MCP, MCPB, phenothiol, mecoprop, fluoroxypyr, triclopyr, clomeprop, naproanilide and the like], (2) herbicidal benzoic acid compounds [2,3,6-TBA, dicamba, clopyralid, picloram, aminopyralid, quinclorac, quinmerac and the like], (3) herbicidal urea compounds [diuron, linuron, chlortoluron, isoproturon, fluometuron, isouron, tebuthiuron, methabenzthiazuron, cumyluron, daimuron, methyl-daimuron and the like], (4) herbicidal triazine compounds [atrazine, ametoryn, cyanazine, simazine, propazine, simetryn, dimethametryn, prometryn, metribuzin, triaziflam and the like], (5) herbicidal bipyridinium compounds [paraquat, diquat and the like], (6) herbicidal hydroxybenzonitrile compounds [bromoxynil, ioxynil and the like], (7) herbicidal dinitroaniline compounds [pendimethalin, prodiamine, trifluralin and the like], (8) herbicidal organophosphorus compounds [amiprofos-methyl, butamifos, bensulide, piperophos, anilofos, glyphosate, glufosinate, glufosinate-P, bialaphos and the like], (9) herbicidal carbamate compounds [di-allate, tri-allate, EPTC, butylate, benthiocarb, esprocarb, molinate, dimepiperate, swep, chlorpropham, phenmedipham, phenisopham, pyributicarb, asulam and the like],

(10) herbicidal acid amide compounds [propanil, propyzamide, bromobutide, etobenzanid and the like],

(11) herbicidal chloroacetoanilide compounds [acetochlor, alachlor, butachlor, dimethenamid, propachlor, metazachlor, metolachlor, pretilachlor, thenylchlor, pethoxamid and the like],

(12) herbicidal diphenylether compounds [acifluorfen-sodium, bifenox, oxyfluorfen, lactofen, fomesafen, chlomethoxynil, aclonifen and the like],

(13) herbicidal cyclic imide compounds [oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, saflufenacil and the like],

(14) herbicidal pyrazole compounds [benzofenap, pyrazolate, pyrazoxyfen, topramezone, pyrasulfotole and the like],

(15) herbicidal triketone compounds [isoxaflutole, benzobicyclon, sulcotrione, mesotrione, tembotrione, tefuryltrione and the like],

(16) herbicidal aryloxyphenoxypropionate compounds [clodinafop-propargyl, cyhalofop-butyl, diclofop-methyl, fenoxaprop-ethyl, fluazifop-butyl, haloxyfop-methyl, quizalofop-ethyl, metamifop and the like],

(17) herbicidal trione oxime compounds [alloxydim-sodium, sethoxydim, butroxydim, clethodim, cloproxydim, cycloxydim, tepraloxydim, tralkoxydim, profoxydim and the like],

(18) herbicidal sulfonylurea compounds [chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, 1-(2-chloro-6-propylimidazo[1,2-a]pyridazin-3-yl-sulfonyl)-3-(4,6-dimethoxypyrimidin-2-yl)urea and the like],

(19) herbicidal imidazolinone compounds [imazamethabenz-methyl, imazamethapyr, imazamox, imazapyr, imazaquin, imazethapyr and the like],

(20) herbicidal sulfonamide compounds [flumetsulam, metosulam, diclosulam, florasulam, cloransulam-methyl, penoxsulam, pyroxsulam and the like],

(21) herbicidal pyrimidinyloxybenzoate compounds [pyrithiobac-sodium, bispyribac-sodium, pyriminobac-methyl, pyribenzoxim, pyriftalid, pyrimisulfan and the like],

(22) other kinds of herbicidal compounds [bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone and the like] and the like.

Examples of the active ingredients of the plant growth regulators include hymexazol, paclobutrazol, uniconazole-P, inabenfide, prohexadione-calcium, aviglycine, naphthaleneacetamide, abscisic acid, indolebutyric acid, ethychlozate, ethephon, cloxyfonac, chlormequat, dichlorprop, gibberellins, prohydrojasmon, benzyladenine, forchlorfenuron, maleic hydrazide, calcium peroxide, mepiquat-chloride, 4-chlorophenoxyacetic acid and the like.

Examples of the active ingredients of the fungicides include:

(1) fungicidal polyhaloalkylthio compounds [captan, folpet and the like], (2) fungicidal organophosphorus compounds [IBP, EDDP, tolclofos-methyl and the like], (3) fungicidal benzimidazole compounds [benomyl, carbendazim, thiophanate-methyl, thiabendazole and the like], (4) fungicidal carboxyamide compounds [carboxin, mepronil, flutolanil, thifluzamid, furametpyr, boscalid, penthiopyrad and the like], (5) fungicidal dicarboxylmide compounds [procymidone, iprodione, vinclozolin and the like], (6) fungicidal acylalanine compounds [metalaxyl and the like], (7) fungicidal azole compounds [triadimefon, triadimenol, propiconazole, tebuconazole, cyproconazole, epoxiconazole, prothioconazole, ipconazole, triflumizole, prochloraz, penconazole, flusilazole, diniconazole, bromuconazole, difenoconazole, metconazole, tetraconazole, myclobutanil, fenbuconazole, hexaconazole, fluquinconazole, triticonazole, bitertanol, imazalil, flutriafol and the like], (8) fungicidal morpholine compounds [dodemorph, tridemorph, fenpropimorph and the like], (9) fungicidal strobilurin compounds [azoxystrobin, kresoxim-methyl, metominostrobin, trifloxystrobin, picoxystrobin, pyraclostrobin, fluoxastrobin, dimoxystrobin and the like],

(10) fungicidal antibiotics [validamycin A, blasticidin S, kasugamycin, polyoxin and the like],

(11) fungicidal dithiocarbamate compounds [mancozeb, maneb, thiuram and the like],

(12) other kinds of fungicidal compounds [fthalide, probenazole, isoprothiolane, tricyclazole, pyroquilon, ferimzone, acibenzolar S-methyl, carpropamid, diclocymet, fenoxanil, tiadinil, diclomezine, teclofthalam, pencycuron, oxolinic acid, TPN, triforine, fenpropidin, spiroxamine, fluazinam, iminoctadine, fenpiclonil, fludioxonil, quinoxyfen, fenhexamid, silthiofam, proquinazid, cyflufenamid, bordeaux mixture, dichlofluanid, cyprodinil, pyrimethanil, mepanipyrim, diethofencarb, pyribencarb, famoxadone, fenamidone, zoxamide, ethaboxam, amisulbrom, iprovalicarb, benthiavalicarb, cyazofamid, mandipropamid, metrafenone, fluopiram, bixafen and the like] and the like.

Examples of the active ingredients of the insecticides include:

(1) insecticidal organophosphorus compounds [fenthion, fenitrothion, pirimiphos-methyl, diazinon, quinalphos, isoxathion, pyridafenthion, chlorpyrifos, chlorpyrifos-methyl, vamidothion, malathion, phenthoate, dimethoate, disulfoton, monocrotophos, tetrachlorvinphos, chlorfenvinphos, propaphos, acephate, trichlorphon, EPN, pyraclofos, butathiofos, chlorethoxyfos, cyanophos, dichlofenthion, dichlorvos, dimethylvinphos, ethion, ethoprophos, etrimfos, formothion, isofenphos, mesulfenfos, methidathion, naled, oxydeprofos, parathion, phosalone, phosmet, profenofos, prothiofos, salithion, sulprofos, tebupirimfos, temephos, terbufos, thiometon, phorate and the like], (2) insecticidal carbamate compounds [carbaryl, metolcarb, isoprocarb, BPMC, propoxur, XMC, carbofuran, carbosulfan, benfuracarb, furathiocarb, methomyl, thiodicarb, alanycarb, bendiocarb, cloethocarb, ethiofencarb, fenobucarb, oxamyl, pirimicarb, xylylcarb, aldicarb and the like], (3) insecticidal synthetic pyrethroid compounds [tefluthrin, bifenthrin, cycloprothrin, ethofenprox, acrinathrin, allethrin, benfluthrin, beta-cyfluthrin, cyfluthrin, cyhalothrin, cypermethrin, deltamethrin, esfenvalerate, fenpropathrin, fenvalerate, flucythrinate, flufenprox, flumethrin, fluvalinate, halfenprox, imiprothrin, permethrin, prallethrin, pyrethrins, resmethrin, sigma-cypermethrin, silafluofen, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, protrifenbute and the like], (4) insecticidal nereistoxin-based compounds [cartap, bensultap, thiocyclam and the like], (5) insecticidal neonicotinoid compounds [imidacloprid, nitenpyram, acetamiprid, thiamethoxam, thiacloprid, dinotefuran, clothianidin and the like], (6) insecticidal benzoylphenylurea compounds [chlorfluazuron, fluazuron, flufenoxuron, hexaflumuron, lufenuron, novaluron, bistrifluoron, diflubenzuron, flucycloxuron, noviflumuron, teflubenzuron, triflumuron and the like], (7) insecticidal macrolide compounds [emamectin, abamectin, milbemectin, lepimectin, spinosad, spinetoram and the like], (8) other kinds of insecticidal compounds [buprofezin, tebufenozide, chromafenozide, halofenozide, methoxyfenozide, fipronil, ethiprole, acetoprole, vaniliprole, pyriprole, pyrafluprole, pymetrozine, pyrifluquinazone, diafenthiuron, indoxacarb, metaflumizone, tolfenpyrad, flufenerim, pyridalyl, flonicamid, spiromesifen, spirotetramat, flubendiamide, chlorantraniliprole, pyriproxyfen, cyromazine, metoxadiazone, triazamate, chlordane, nicotine-sulfate, tralopyril, Bt toxins and the like] and the like.

Examples of the active ingredients of the acaricides include hexythiazox, pyridaben, fenpyroximate, tebufenpyrad, chlorfenapyr, etoxazole, pyrimidifen, acequinocyl, bifenazate, spirodiclofen, fenazaquin, bromopropylate, formetanate, amitraz, benzoximate, chinomethionat, chlorobenzilate, chlorfenson, clofentezine, cyflumetofen, dicofol, fenbutatin oxide, fenothiocarb, fluacrypyrim, propargite, polynactins, tetradifon, amidoflumet, cyenopyrafen and the like.

Examples of the active ingredients of the nematocides include fosthiazate, cadusafos, benclothiaz, metam-ammonium, metam-sodium, DCIP, levamisol, methyl isothiocyanate, morantel tartrate, imicyafos and the like.

The herbicide of the present invention may further contain a safener (for example, furilazole, dichlormid, benoxacor, allidochlor, isoxadifen-ethyl, fenchlorazole-ethyl, mefenpyrdiethyl, cloquintocet-mexyl, fenclorim, cyprosulfamide, cyometrinil, oxabetrinil, fluxofenim, flurazole, 2-dichloromethyl-2-methyl-1,3-dioxolane, 1,8-naphthalic anhydride and the like), a coloring agent, a fertilizer (for example, urea and the like) and the like, if necessary.

The compound of the present invention can be used as an active ingredient of a herbicide for croplands such as fields, paddy fields, lawns, and orchards, or non-croplands. The compound of the present invention can control weeds in croplands and the like where "crop plants" are cultivated, without causing any injury to "crop plants".

Examples of the "crop plants" include:

agricultural crops: maize, rice, wheat, barley, rye, oat, sorghum, cotton, soybean, peanut, buckwheat, sugar beet, rape, sunflower, sugarcane, tobacco and the like;

vegetables: solanaceous vegetables (for example, egg plant, tomato, green pepper, red pepper, potato and the like), cucurbitaceous vegetables (for example, cucumber, pumpkin, zucchini, watermelon, melon and the like), brassicaceous vegetables (for example, Japanese radish, turnip, horseradish, kohlrabi, Chinese cabbage, cabbage, leaf mustard, broccoli, cauliflower and the like), compositae vegetables (for example, burdock, garland chrysanthemum, artichoke, lettuce and the like), liliaceae vegetables (for example, leek, onion, garlic, asparagus and the like), umbelliferous vegetables (for example, carrot, parsley, celery, wild parsnip and the like), chenopodiaceous vegetables (for example, spinach, Swiss chard and the like), labiatae vegetables (for example, perilla, mint, basil and the like), strawberry, sweet potato, Japanese yam, taro, and the like;

fruits: pomaceous fruits (for example, apple, pear, Japanese pear, Chinese quince, quince and the like), stone fruits (for example, peach, plum, nectarine, Japanese plum, mahaleb cherry, apricot, prune and the like), citrus fruits (for example, tangerine, orange, lemon, lime, grapefruit and the like), nuts (for example, chestnut, walnut, hazel, almond, pistachio, cashew nut, macadamia nut and the like), berries (for example, blueberry, cranberry, blackberry, raspberry and the like), grape, persimmon, olive, loquat, banana, coffee, date palm, coconut palm, oil palm and the like;

trees other than fruit trees: tea plant, mulberry, flowering plants, roadside trees (for example, ash plant, birch, American dogwood, eucalyptus, ginkgo, lilac, maple, willow oak, poplar, cercis, liquidambar, plane tree, zelkova, thuja, Abies, hemlock spruce, needle juniper, pine, spruce fir, yew) and the like; and others: flowers (for example, rose, carnation, chrysanthemum, prairie gentian, gypsophila, gerbera, marigold, salvia, pethunia, verbena, tulip, aster, gentian, lily, pansy, cyclamen, orchid, convallaria, lavender, stock, ornamental cabbage, primula, poinsettia, gladiolus, cattleya, daisy, cymbidium, begonia and the like), ornamental plants, and the like.

The above "crop plants" include those which are conferred resistance to herbicides including HPPD inhibitors such as isoxaflutole; ALS inhibitors such as imazethapyr and thifensulfuron-methyl; EPSP synthase inhibitors such as glyphosate; glutamine synthetase inhibitors such as glufosinate; acetyl CoA carboxylase inhibitors such as sethoxydim; PPO inhibitor such as flumioxazin; bromoxynil, dicamba and 2,4-D by classic breeding technique, a genetic engineering technique or the like.

Examples of the "crop plants" to which herbicidal resistance is given by a classic breeding technique include rape, wheat, sunflower, rice and corn having resistance to imidazolinone ALS inhibitor herbicides such as imazethapyr, which are already on the market under the name of Clearfield (registered trademark); soybean resistant to sulfonylurea ALS inhibitor herbicides such as thifensulfuron-methyl, which is already on the market under the name of STS soybean; and crop plants resistant to acetyl CoA carboxylase inhibitors such as trione oxime herbicides and aryloxyphenoxypropionate herbicides, for example, SR corn. The crop plants to which the resistance to acetyl CoA carboxylase inhibitors is given are described in, for example, Proc. Natl. Acad. Sci. USA, vol. 87, pp. 7175-7179 (1990).

In addition, mutant acetyl CoA carboxylase which is resistant to acetyl CoA carboxylase inhibitors is described, for example, in Weed Science vol. 53, pp. 728-746 (2005). A gene for such mutant acetyl CoA carboxylase can be introduced into a crop plant by a genetic engineering technique or a mutation involved in the resistance to acetyl CoA carboxylase inhibitors can be introduced into an acetyl CoA carboxylase-coding gene of a crop plant to produce a crop plant with resistance to acetyl CoA carboxylase inhibitors.

Further, nucleic acids for introduction of a base substitution mutation can be introduced into the cell of a crop plant by chimeraplasty (see, Gura T., "Repairing the Genome's Spelling Mistakes", Science, vol. 285, pp. 316-318 (1999)) to induce a site-directed amino acid mutation in the gene of the crop plant which is targeted by a herbicide, and thereby a crop plant resistant to the herbicide can be produced.

Examples of the "crop plants" to which herbicidal resistance is conferred by a genetic engineering technique include corn, soybean, cotton, rape and sugar beet varieties having resistance to glyphosate, which are already on the market under the product name of Roundup Ready (registered trademark) or Agrisure (registered trademark) GT; corn, soybean, cotton and rape varieties having resistance to glufosinate, which are already on the market under the product name of Liberty Link (registered trademark); and a cotton variety having bromoxynil resistance, which is already on the market under the product name of BXN.

The above "crop plants" also include crop plants conferred an ability to produce insecticidal toxins known as selective toxins produced from *Bacillus* bacteria which ability is given by a genetic engineering technique.

Examples of such insecticidal toxins include insecticidal proteins produced from *Bacillus cereus* or *Bacillus popilliae*; δ-endotoxins such as Cry1Ab, Cry1Ac, Cry1F, Cry1Fa2, Cry2Ab, Cry3A, Cry3Bb1 and Cry9C produced from *Bacillus thuringiensis*; insecticidal proteins such as VIP1, VIP2, VIP3 and VIP3A; insecticidal proteins produced from nematode; toxins produced by animals such as a scorpion toxin, a spider toxin, a bee toxin and an insect specific nervous system toxin; filamentous fungus toxins; plant lectins; agglutinins; protease inhibitors such as trypsin inhibitors, serine protease inhibitors, patatin, cystatin and papain inhibitors; ribosome inactivation proteins (RIP) such as ricins, corn-RIP, abrins, luffin, saporins, and bryodin; steroid metabolism enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel and calcium channel inhibitors; Juvenile hormone esterase; diuretic hormone receptors; stilbene synthase; bibenzyl synthase; chitinase; glucanases; and the like.

Further examples of such insecticidal toxins include hybrid toxins of the above insecticidal proteins (for example, Cry1Ab, Cry1Ac, Cry1F, Cry1Fa2, Cry2Ab, Cry3A, Cry3Bb1, Cry9C, VIP1, VIP2, VIP3, VIP3A) and insecticidal proteins in which a part of amino acids constituting the insecticidal proteins is deleted or modified. The hybrid toxins are created by combining different domains of the above insecticidal proteins by a genetic engineering technique. An example of the toxin in which a part of amino acids constituting the insecticidal protein is deleted includes Cry1Ab in which a part of amino acids is deleted. An example of the toxin in which a part of amino acids constituting the insecticidal protein is modified is made by substitution of one or more amino acids of a natural toxin.

The insecticidal toxins and genetically modified crop plants which have the ability to produce the insecticidal toxins are described, for example, in EP-A-0374753, WO 93/07278, WO 95/34656, EP-A-0427529, EP-A-451878 and WO 03/052073.

The "crop plants" which are given the ability to produce the insecticidal toxins by a genetic engineering technique have resistance to attack by Coleopteran pests, Dipteran pests and/or Lepidopteran pests.

Genetically modified plants having one or more insect-resistant genes and expressing one or more insecticidal toxins are already known, and some of them are commercially available. Examples of such genetically modified plants include YieldGard (registered trademark) (a corn variety expressing Cry1Ab toxin), YieldGard Rootworm (registered trademark) (a corn variety expressing Cry3Bb1 toxin), YieldGard Plus (registered trademark) (a corn variety expressing Cry1Ab and Cry3Bb1 toxins), Herculex I (registered trademark) (a corn variety expressing Cry1Fa2 toxin and phosphinothricin N-acetyltransferase (PAT) to confer resistance to glufosinate), NuCOTN33B (registered trademark) (a cotton variety expressing Cry1Ac toxin), Bollgard I (registered trademark) (a cotton variety expressing Cry1Ac toxin), Bollgard II (registered trademark) (a cotton variety expressing Cry1Ac and Cry2Ab toxins), VIPCOT (registered trademark) (a cotton variety expressing VIP toxin), NewLeaf (registered trademark) (a potato variety expressing Cry3A toxin), NatureGard (registered trademark), Agrisure (registered trademark) GT Advantage (GA21 glyphosate-resistance trait), Agrisure (registered trademark) CB Advantage (Bt11 corn borer (CB) trait), and Protecta (registered trademark).

The above "crop plants" also include those which are given an ability to produce anti-pathogen substances by a genetic engineering technique.

Examples of the anti-pathogen substances include PR proteins (PRPs, described in EP-A-0392225); ion channel inhibitors such as sodium channel inhibitors, and calcium channel inhibitors (KP1, KP4 and KP6 toxins and the like produced by virus are known); stilbene synthase; bibenzyl synthase; chitinase; glucanase; microorganism-producing substances such as peptide antibiotics, antibiotics having a heterocycle, and protein factors relating to resistance against plant pathogens (described in WO 03/000,906), and the like. Such anti-pathogen substances and genetically modified plants capable of producing them are described, for example, in EP-A-0392225, WO 95/33818 and EP-A-0353191.

The above "crop plants" also include those to which a beneficial trait such as a modified oil component or an enhanced amino acid content are given by a genetic engineering technique. Examples of such crop plants include VISTIVE (registered trademark) (low linolenic soybean which has a reduced content of linolenic acid), and high-lysine (high-oil) corn (corn which has an increased content of lysine or oil).

Furthermore, the above "crop plants" include stacked crop plant varieties which have a combination of two or more of beneficial traits such as the above-described classical herbicide-resistant trait, a herbicide-resistance gene, a pest-resistant insecticidal gene, an anti-pathogen substance-producing gene, a modified oil component, and an enhanced amino acid content.

When the compound of the present invention is used for a herbicide-resistant crop plant, the plant is treated sequentially with the compound of the present invention and the herbicide (e.g., glyphosate or a salt thereof, glufosinate or a salt thereof, dicamba or a salt thereof, imazethapyr or a salt thereof, isoxaflutole, etc.) to which the plant is resistant, or with a mixture of both, and thereby comprehensive weed control can be attained.

The compound of the present invention can be produced, for example, by following preparation methods.

Preparation Method 1

A compound represented by the formula (I-a), which is a compound of the present invention wherein G is a hydrogen atom, can be prepared by reacting a compound represented by the formula (II) with a metal hydroxide.

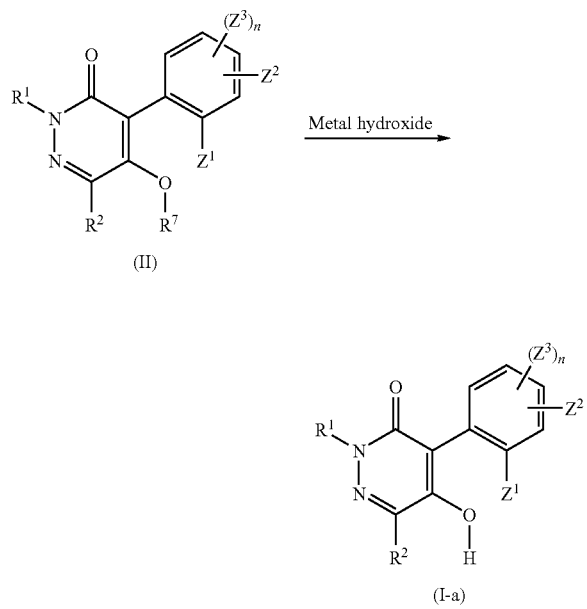

(II)

(I-a)

wherein $R^7$ represents a $C_{1-6}$ alkyl group (for example, a methyl group or an ethyl group), and $R^1$, $R^2$, $Z^1$, $Z^2$, $Z^3$ and n are as defined above.

The reaction is generally performed in a solvent. Examples of the solvent used in the reaction include water; ethers such as tetrahydrofuran and dioxane; and a mixture thereof.

Examples of the metal hydroxide used in the reaction include alkali metal hydroxides such as sodium hydroxide and potassium hydroxide. The amount of the metal hydroxide used in the reaction is generally 1 to 120 molar equivalents, preferably 1 to 40 molar equivalents to the compound represented by the formula (II).

The reaction temperature is generally in the range from room temperature to the boiling point of the solvent, preferably at the boiling, point of the solvent. The reaction can be also performed in a sealed tube or a high pressure resistant closed vessel while heating. The reaction time is generally from 5 minutes to a few weeks.

The completion of the reaction can be confirmed by an analytical means such as thin layer chromatography, high performance liquid chromatography or the like after sampling a part of a reaction mixture. After the completion of the reaction, the compound represented by the formula (I-a) can be isolated, for example, by neutralizing the reaction mixture with an addition of an acid, mixing the reaction mixture with water followed by extraction with an organic solvent, and then drying and concentrating the resulting organic layer.

Preparation Method 2

A compound represented by the formula (I-b), which is a compound of the present invention wherein G is a group other than a hydrogen atom, can be prepared by reacting a compound represented by the formula (I-a) with a compound represented by the formula (III).

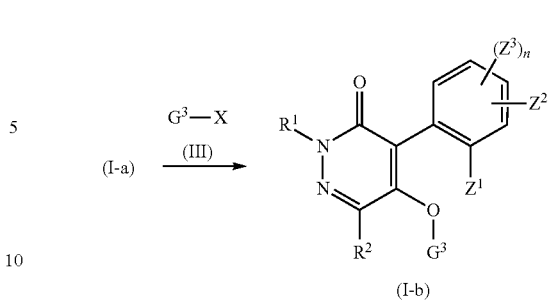

(I-b)

wherein $G^3$ is as defined for G, provided that a hydrogen atom is excluded; X represents a halogen atom (for example, a chlorine atom, a bromine atom, or an iodine atom) or a group represented by the formula $OG^3$; and $R^1$, $R^2$, $Z^1$, $Z^2$, $Z^3$ and n are as defined above.

The reaction can be performed in a solvent. Examples of the solvent in the reaction include aromatic hydrocarbons such as benzene and toluene; ethers such as diethyl ether, isopropyl ether, dioxane, tetrahydrofuran and dimethoxyethane; halogenated hydrocarbons such as dichloromethane, chloroform and 1,2-dichloroethane; amides such as dimethylformamide and dimethylacetamide; sulfoxides such as dimethylsulfoxide; sulfones such as sulfolane; and a mixture thereof.

Examples of the compound represented by the formula (III) include carboxylic acid halides such as acetyl chloride, propionyl chloride, isobutyryl chloride, pivaloyl chloride, benzoyl chloride and cyclohexane carboxylic acid chloride; carboxylic acid anhydrides such as acetic anhydride and trifluoroacetic anhydride; carbonate half ester halides such as methyl chloroformate, ethyl chloroformate and phenyl chloroformate; carbamoyl halides such as dimethylcarbamoyl chloride; sulfonic acid halides such as methanesulfonyl chloride and p-toluenesulfonyl chloride; sulfonic acid anhydrides such as methanesulfonic anhydride and trifluoromethanesulfonic anhydride; and halogenated phosphate esters such as dimethyl chlorophosphate. The amount of the compound represented by the formula (III) used in the reaction is generally 1 molar equivalent or more, preferably 1 to 3 molar equivalents to the compound represented by the formula (I-a).

The reaction is generally performed in the presence of a base. Examples of the base used in the reaction include organic bases such as triethylamine, tripropylamine, pyridine, dimethylaminopyridine and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate and sodium hydride. The amount of the base used in the reaction is generally 0.5 to 10 molar equivalents, preferably 1 to 5 molar equivalents to the compound represented by the formula (I-a).

The reaction temperature is generally at −30 to 180° C., preferably at −10 to 50° C. The reaction time is generally from 10 minutes to 30 hours.

The completion of the reaction can be confirmed by an analytical means such as thin layer chromatography, high performance liquid chromatography or the like after sampling a part of a reaction mixture. After the completion of the reaction, the compound represented by the formula (I-b) can be isolated, for example, by mixing the reaction mixture with water followed by extraction with an organic solvent, and then drying and concentrating the resulting organic layer.

The compound represented by the formula (III) is a known compound, or can be prepared from a known compound.

Preparation Method 3

A compound represented by the formula (I-a), which is a compound of the present invention wherein G is a hydrogen atom, can be also prepared by treating a compound represented by the formula (VI) with a base.

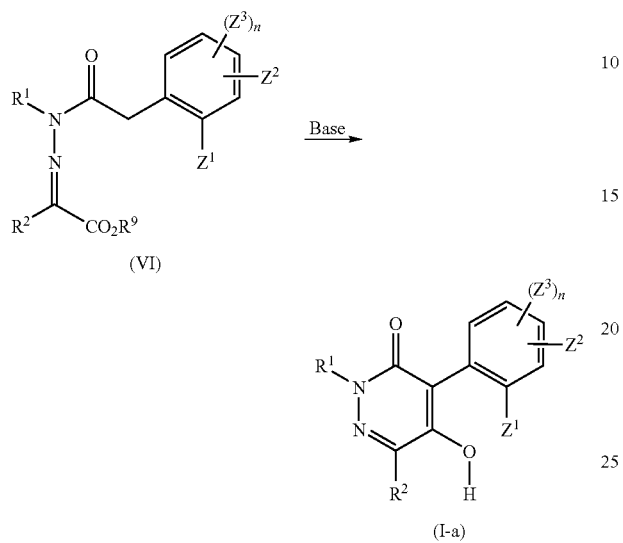

(VI)

(I-a)

wherein $R^9$ represents a $C_{1-6}$ alkyl group (for example, a methyl group or an ethyl group), and $R^1$, $R^2$, $Z^1$, $Z^2$, $Z^3$ and n are as defined above.

The reaction is generally performed in a solvent. Examples of the solvent in the reaction include aromatic hydrocarbons such as benzene, toluene and xylene; ethers such as diethyl ether, isopropyl ether, dioxane, tetrahydrofuran and dimethoxyethane; halogenated hydrocarbons such as dichloromethane, chloroform and 1,2-dichloroethane; amides such as dimethylformamide and dimethylacetamide; sulfones such as sulfolane; and a mixture thereof.

Examples of the base in the reaction include metal alkoxides such as potassium tert-butoxide; alkali metal hydride such as sodium hydride; and organic bases such as triethylamine, tributylamine and N,N-diisopropylethylamine. The amount of the base used in the reaction is generally 1 to 10 molar equivalents, preferably 2 to 5 molar equivalents to the compound represented by the formula (VI).

The reaction temperature is generally at −60 to 180° C., preferably at −10 to 100° C. The reaction time is generally from 10 minutes to 30 hours.

The completion of the reaction can be confirmed by an analytical means such as thin layer chromatography, high performance liquid chromatography or the like after sampling a part of reaction mixture. After the completion of the reaction, the compound represented by the formula (I-a) can be isolated, for example, by neutralizing the reaction mixture with an addition of an acid, mixing the reaction mixture with water followed by extraction with an organic solvent, and then drying and concentrating the resulting organic layer.

Preparation Method 4

Among the compounds of the present invention represented by the formula (I-a), a compound represented by the following formula (I-a-x) can be also prepared by the following method.

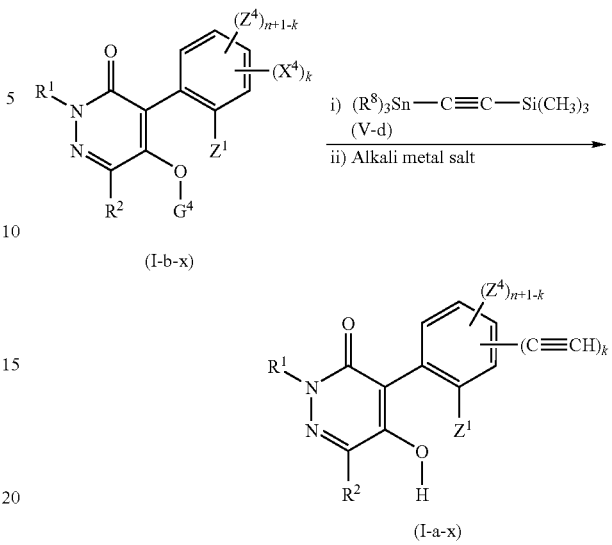

(I-b-x)

(I-a-x)

wherein $X^4$ represents a halogen atom (for example, a chlorine atom, a bromine atom, or an iodine atom); $R^8$ represents a $C_{1-6}$ alkyl group (for example, a methyl group, or a butyl group); $Z^4$ is as defined for $Z^3$, provided that a $C_{2-6}$ alkynyl group, a halogen atom, a $C_{6-10}$ aryl group substituted with at least one halogen atom and a 5- or 6-membered heteroaryl group substituted with at least one halogen atom are excluded; k represents 1, 2, 3 or 4; $G^4$ represents a $C_{1-6}$ alkylcarbonyl group or a $C_{1-6}$ alkyloxycarbonyl group; and $R^1$, $R^2$, $Z^1$ and n are as defined above.

In the reaction, a compound represented by the formula (I-b-x) and an organometallic reagent represented by the formula (V-d) are subjected to coupling reaction, followed by reaction with an alkali metal salt to remove a trimethylsilyl group and to convert the substituent $G^4$ into a hydrogen atom. Thus the compound represented by the formula (I-a-x) can be prepared.

The first step of the reaction using the compound represented by the formula (V-d) is performed in a solvent. Examples of the solvent include aromatic hydrocarbons such as benzene and toluene; ethers such as diethyl ether, diisopropyl ether, dioxane, tetrahydrofuran and dimethoxyethane; halogenated hydrocarbons such as chloroform and 1,2-dichloroethane; amides such as dimethylformamide, dimethylacetamide, etc.; and a mixture thereof.

In the first step of the reaction, the organometallic reagent represented by the formula (V-d) can be generally used in an amount of k molar equivalents or more, preferably 1 to 10 molar equivalents to the compound represented by the formula (I-b-x).

The first step of the reaction is carried out in the presence of a catalyst. Examples of the catalyst include palladium catalysts such as tetrakis(triphenylphosphine)palladium and dichlorobis(triphenylphosphine)palladium. The amount of the catalyst used in the reaction is generally 0.001 to 0.5 molar equivalents, preferably 0.01 to 0.2 molar equivalents to the compound represented by the formula (I-b-x).

The reaction temperature of the first step of the reaction is generally at −80 to 180° C., preferably at −30 to 150° C. The reaction time of the first step of the reaction is generally from 30 minutes to 100 hours.

The completion of the reaction can be confirmed by an analytical means such as thin layer chromatography, high performance liquid chromatography or the like after sampling a part of a reaction mixture. After the completion of the reaction, a product from the first step of the reaction can be isolated, for example, by subjecting the reaction mixture to concentration, chromatographic purification and the like.

The organometallic reagent represented by the formula (V-d) is a known compound, or can be prepared from a known compound in accordance with a known method.

The second step of the reaction using an alkali metal salt is carried out in a solvent. Examples of the solvent include water; alcohols such as methanol and ethanol; ethers such as dioxane, tetrahydrofuran and dimethoxyethane; and a mixture thereof.

Examples of the alkali metal salt used for the second step of the reaction include alkali metal hydroxides such as sodium hydroxide and potassium hydroxide; and alkali metal carbonates such as sodium carbonate and potassium carbonate. In the second step of the reaction, the amount of the alkali metal salt is generally (1+k) molar equivalents or more, preferably 2 to 10 molar equivalents to the compound represented by the formula (I-b-x).

The reaction temperature of the second step of the reaction is generally at −30 to 180° C., preferably at −10 to 50° C. The reaction time of the second step of the reaction is generally from 30 minutes to 100 hours.

The completion of the reaction can be confirmed by an analytical means such as thin layer chromatography, high performance liquid chromatography or the like after sampling a part of a reaction mixture. After the completion of the reaction, the compound represented by the formula (I-a-x) can be isolated, for example, by mixing the reaction mixture with water, neutralizing the reaction mixture with an addition of an acid followed by extraction with an organic solvent, and then drying and concentrating the resulting organic layer.

Preparation Method 5

Among the compounds of the present invention represented by the formula (I-a), a compound represented by the following formula (I-a-y) can be also prepared by the following method.

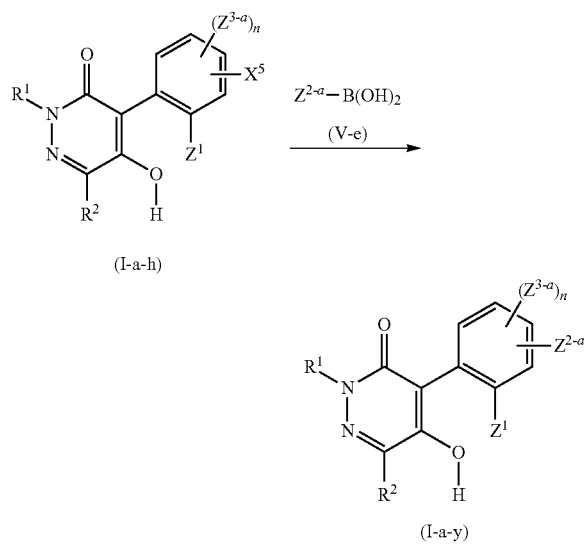

wherein $X^5$ represents a halogen atom (for example, a chlorine atom, a bromine atom, or an iodine atom); $Z^{3-a}$ is as defined for $Z^3$, provided that a halogen atom, a $C_{6-10}$ aryl group substituted with at least one halogen atom and 5- or 6-membered heteroaryl group substituted with at least one halogen atom are excluded; $Z^{2-a}$ represents a $C_{3-8}$ cycloalkyl group, a $C_{6-10}$ aryl group or a 5- or 6-membered heteroaryl group (each of these may be substituted with at least one group selected from the group consisting of a halogen atom and a $C_{1-6}$ alkyl group); and $R^1$, $R^2$, $Z^1$ and n are as defined above.

In the reaction, a compound represented by the formula (I-a-h) and an organometallic reagent represented by the formula (V-e) are subjected to coupling reaction to prepare a compound represented by the formula (I-a-y).

In the reaction, the organometallic reagent represented by the formula (V-e) can be used generally in an amount of 1 molar equivalent or more, preferably 1 to 3 molar equivalents to the compound represented by the formula (I-a-h).

The reaction is carried out in a solvent. Examples of the solvent in the reaction include aromatic hydrocarbons such as benzene and toluene; alcohols such as methanol, ethanol and propanol; ethers such as diethyl ether, diisopropyl ether, dioxane, tetrahydrofuran, and dimethoxyethane; ketones such as acetone and methyl ethyl ketone; amides such as dimethylformamide and dimethylacetamide; sulfoxides such as dimethyl sulfoxide; sulfones such as sulfolane; water; and a mixture thereof.

The reaction is performed in the presence of a base. Examples of the base in the reaction include organic bases such as triethylamine, tripropylamine, pyridine, dimethylaniline, dimethylaminopyridine and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, cesium carbonate and potassium phosphate. The amount of the base is generally 0.5 to 10 molar equivalents, preferably 1 to 5 molar equivalents to the compound represented by the formula (I-a-h).

Further, the reaction is carried out in the presence of a catalyst. Examples of the catalyst in the reaction include palladium catalysts such as tetrakis(triphenylphosphine)palladium, dichlorobis(triphenylphosphine)palladium and dichlorobis(tricyclohexylphosphine)palladium. The amount of the catalyst used in the reaction is generally 0.001 to 0.5 molar equivalents, preferably 0.01 to 0.2 molar equivalents to the compound represented by the formula (I-a-h).

The reaction temperature of the reaction is generally at 20 to 180° C., preferably at 60 to 150° C. The reaction time is generally from 30 minutes to 100 hours.

The completion of the reaction can be confirmed by an analytical means such as thin layer chromatography, high performance liquid chromatography or the like after sampling a part of a reaction mixture. After the completion of the reaction, the compound represented by the formula (I-a-y) can be isolated, for example, by mixing the reaction mixture with water, neutralizing the reaction mixture with an addition of an acid followed by extraction with an organic solvent, and then drying and concentrating the resulting organic layer.

The organometallic reagent represented by the formula (V-e) is a known compound, or can be prepared from a known compound in accordance with a known method.

Each compound prepared by the Preparation Methods 1 to 5 may be also isolated and/or purified by other known methods, such as concentration, concentration under reduced pressure, extraction, dissolution in different solvents, crystallization, recrystallization, chromatography and the like.

Next, specific examples of the compound of the present invention are shown below.
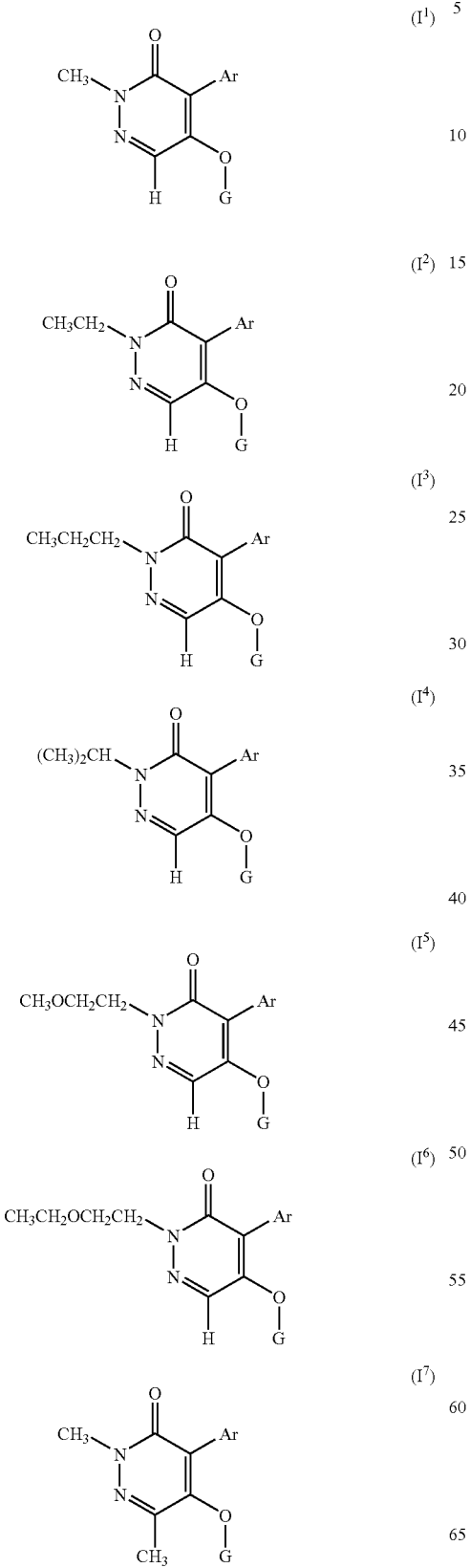
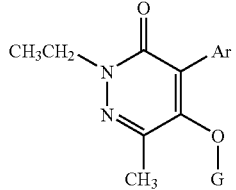
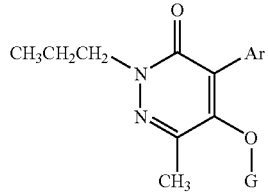
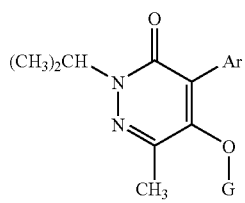
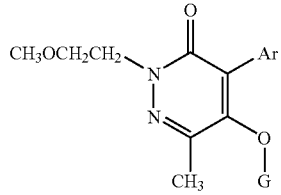
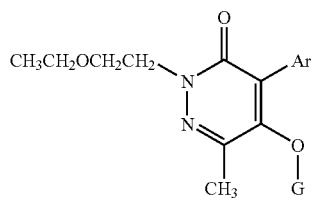
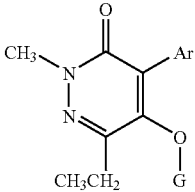
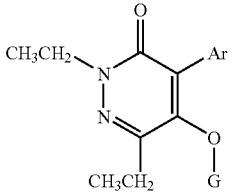

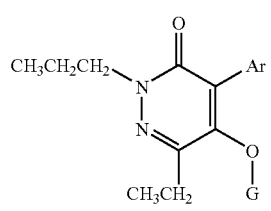
(I¹⁵)
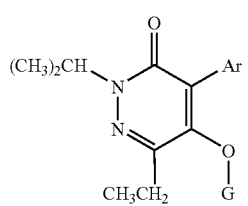
(I¹⁶)
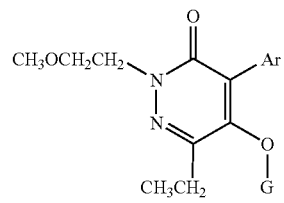
(I¹⁷)
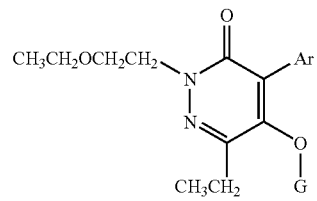
(I¹⁸)
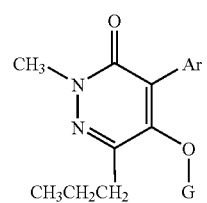
(I¹⁹)
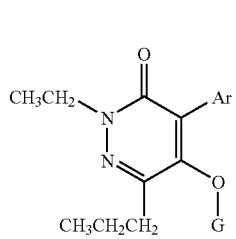
(I²⁰)
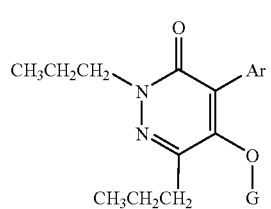
(I²¹)
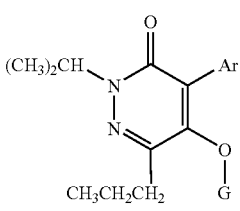
(I²²)
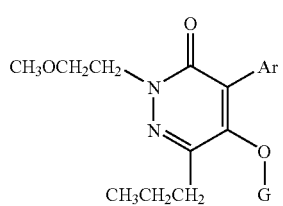
(I²³)
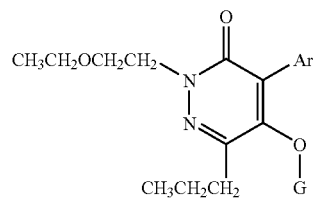
(I²⁴)
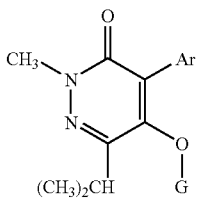
(I²⁵)
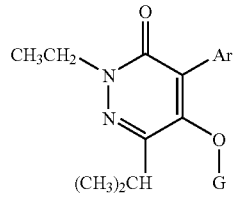
(I²⁶)
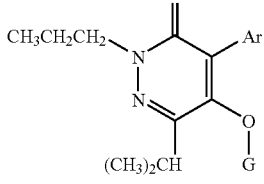
(I²⁷)
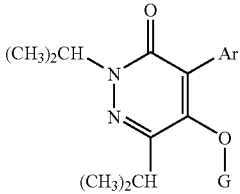
(I²⁸)

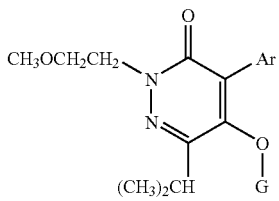

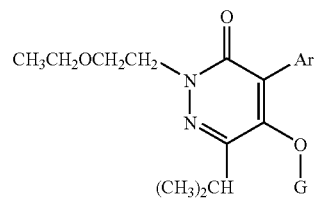

1) The pyridazinone compounds represented by any of the formulas (I¹) to (I³⁰), wherein Ar is a 4-chloro-2,6-diethylphenyl group, and G is a hydrogen atom, an acetyl group, a trifluoroacetyl group, a propionyl group, a butyryl group, an isobutyryl group, an isovaleryl group, pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

2) The pyridazinone compounds represented by any of the formulas (I¹) to (I³⁰), wherein Ar is a 4-bromo-2,6-diethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

3) The pyridazinone compounds represented by any of the formulas (I¹) to (I³⁰), wherein Ar is a 4-cyano-2,6-diethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

4) The pyridazinone compounds represented by any of the formulas (I¹) to (I³⁰), wherein Ar is a 2,6-diethyl-4-methoxyphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

5) The pyridazinone compounds represented by any of the formulas (I¹) to (I³⁰), wherein Ar is a 2,6-diethyl-4-nitrophenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

6) The pyridazinone compounds represented by any of the formulas (I¹) to (I³⁰), wherein Ar is a 2,6-diethyl-4-phenylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

7) The pyridazinone compounds represented by any of the formulas (I¹) to (I³⁰), wherein Ar is a 2,6-diethyl-4-ethynylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

8) The pyridazinone compounds represented by any of the formulas (I¹) to (I³⁰), wherein Ar is a 2-cyano-4,6-dimethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

9) The pyridazinone compounds represented by any of the formulas (I¹) to (I³⁰), wherein Ar is a 2-cyano-6-ethyl-4-methylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

10) The pyridazinone compounds represented by any of the formulas (I¹) to (I³⁰), wherein Ar is a 2,4-dichloro-6-methylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, dimethylaminocarbonyl group, a methanesulfonyl group, a trifluoromethanesulfonyl group, a benzenesulfonyl group or a p-toluenesulfonyl group.

11) The pyridazinone compounds represented by any of the formulas (I¹) to (I³⁰), wherein Ar is a 2-chloro-4,6-dimethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

12) The pyridazinone compounds represented by any of the formulas (I¹) to (I³⁰), wherein Ar is a 2-chloro-6-ethyl-4-methylphenyl group, and G is a hydrogen atom, an acetyl group, a trifluordacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

13) The pyridazinone compounds represented by any of the formulas ($I^1$) to ($I^{30}$), wherein Ar is a 2,4-dichloro-6-ethylphenyl group, and G is a hydrogen atom, an acetyl group, a trifluoroacetyl group, a propionyl group, butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

14) The pyridazinone compounds represented by any of the formulas ($I^1$) to ($I^{30}$), wherein Ar is a 2-bromo-6-ethyl-4-methylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, dimethylaminocarbonyl group, a methanesulfonyl group, a trifluoromethanesulfonyl group, a benzenesulfonyl group or a p-toluenesulfonyl group.

15) The pyridazinone compounds represented by any of the formulas ($I^1$) to ($I^{30}$), wherein Ar is a 4-chloro-2-ethyl-6-methoxyphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

16) The pyridazinone compounds represented by any of the formulas ($I^1$) to ($I^{30}$), wherein Ar is a 2-chloro-6-methoxy-4-methylphenyl group, and G is a hydrogen atom, an acetyl group, a trifluoroacetyl group, a propionyl group, a butyryl group, an isobutyryl group, an isovaleryl group, pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

17) The pyridazinone compounds represented by any of the formulas ($I^1$) to ($I^{30}$), wherein Ar is a 2-ethyl-6-methoxy-4-methylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

18) The Pyridazinone compounds represented by any of the formulas ($I^1$) to ($I^{30}$), wherein Ar is a 4-(4-chlorophenyl)-2,6-diethylphenyl group, and G is a hydrogen atom, an acetyl group, a trifluoroacetyl group, propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

19) The pyridazinone compounds represented by any of the formulas ($I^1$) to ($I^{30}$), wherein Ar is a 2,6-diethyl-4-(4-methylphenyl)phenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

20) The pyridazinone compounds represented by any of the formulas ($I^1$) to ($I^{30}$), wherein Ar is a 2-ethyl-6-ethynyl-4-phenylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

21) The pyridazinone compounds represented by any of the formulas ($I^1$) to ($I^{30}$), wherein Ar is a 2-ethyl-6-methoxy-4-phenylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

22) The pyridazinone compounds represented by any of the formulas ($I^1$) to ($I^{30}$), wherein Ar is a 2-chloro-6-ethyl-4-phenylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

23) The pyridazinone compounds represented by any of the formulas ($I^1$) to ($I^{30}$), wherein Ar is a 2,6-diethyl-4-trifluoromethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

24) The pyridazinone compounds represented by any of the formulas ($I^1$) to ($I^{30}$), wherein Ar is a 2,6-diethyl-4-trifluoromethoxyphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycar- 25) The pyridazinone compounds represented by any of the formulas (I¹) to (I³⁰), wherein Ar is a 2-ethyl-6-ethynyl-4-methylphenyl group, and G is a hydrogen atom, an acetyl group, a trifluoroacetyl group, a propionyl group, a butyryl group; an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

26) The pyridazinone compounds represented by any of the formulas (I¹) to (I³⁰), wherein Ar is a 2-chloro-6-ethyl-4-methoxyphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

27) The pyridazinone compounds represented by any of the formulas (I¹) to (I³⁰), wherein Ar is a 2-cyclopropyl-6-ethyl-4-methylphenyl group, and G is a hydrogen atom, an acetyl group, a trifluoroacetyl group, propionyl group, butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

28) The pyridazinone compounds represented by any of the formulas (I¹) to (I³⁰), wherein Ar is a 4-cyclopropyl-2,6-diethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

29) The pyridazinone compounds represented by any of the formulas (I¹) to (I³⁰), wherein Ar is a 5-(4-chlorophenyl)-2-methylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

30) The pyridazinone compounds represented by any of the formulas (I¹) to (I³⁰), wherein Ar is a 5-(4-fluorophenyl)-2-methylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

31) The pyridazinone compounds represented by any of the formulas (I¹) to (I³⁰), wherein Ar is a 2-bromo-4,6-dimethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

32) The pyridazinone compounds represented by any of the formulas (I¹) to (I³⁰), wherein Ar is a 2-methoxy-4,6-dimethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

33) The pyridazinone compounds represented by any of the formulas (I¹) to (I³⁰), wherein Ar is a 2-ethynyl-4,6-dimethylphenyl group, and G is a hydrogen atom, an acetyl group, a trifluoroacetyl group, a propionyl group, a butyryl group, an isobutyryl group, an isovaleryl group, a pivaloyl group, a cyclohexylcarbonyl group, a benzoyl group, a benzylcarbonyl group, a methoxycarbonyl group, an ethoxycarbonyl group, a phenoxycarbonyl group, a dimethylaminocarbonyl group, a methanesulfonyl group, a trifluoromethanesulfonyl group, a benzenesulfonyl group or a p-toluenesulfonyl group.

The present invention also includes useful intermediate compounds for production of the compound represented by the formula (I-a), the compound represented by the formula (II) and the compound represented by the formula (VI).

Reference Preparation Method 1

The compound represented by the formula (II) can be produced, for example, by the following method.

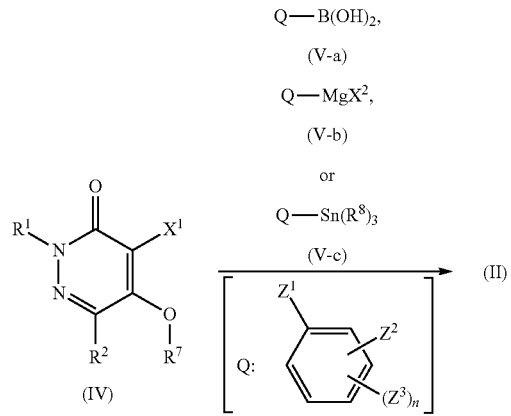

wherein $X^1$ represents a leaving group (for example, a halogen atom such as a chlorine atom, a bromine atom, or an iodine atom), $X^2$ represents a halogen atom (for example, a chlorine atom, a bromine atom or an iodine atom), and $R^1$, $R^2$, $R^7$, $R^8$, $Z^1$, $Z^2$, $Z^3$ and n are as defined above.

In the reaction, the compound represented by the formula (IV) can be subjected to coupling reaction with an organometallic reagent represented by the formula (V-a), (V-b) or (V-c)

(generally 1 molar equivalent or more, preferably 1 to 3 molar equivalents to the compound represented by the formula (IV)) to prepare the compound represented by the formula (II).

The reaction using the compound represented by the formula (V-a) is performed in a solvent. Examples of the solvent include aromatic hydrocarbons such as benzene and toluene; alcohols such as methanol, ethanol and propanol; ethers such as diethyl ether, isopropyl ether, dioxane, tetrahydrofuran and dimethoxyethane; ketones such as acetone and methyl ethyl ketone; amides such as dimethylformamide and dimethylacetamide; sulfoxides such as dimethylsulfoxide; sulfones such as sulfolane; water; and a mixture thereof.

The reaction using the compound represented by the formula (V-a) is performed in the presence of a base. Examples of the base include organic bases such as triethylamine, tripropylamine, pyridine, dimethylaniline, dimethylaminopyridine and 1,8-diazabicyclo[5.4.0]-7-undecene; and inorganic bases such as sodium hydroxide, potassium hydroxide, calcium hydroxide, sodium carbonate, potassium carbonate, sodium hydrogen carbonate, calcium carbonate, cesium carbonate and potassium phosphate. The amount of the base is generally 0.5 to 10 molar equivalents, preferably 1 to 5 molar equivalents to the compound represented by the formula (IV).

Further, the reaction using the compound represented by the formula (V-a) is performed in the presence of a catalyst. Examples of the catalyst include palladium catalysts such as tetrakis(triphenylphosphine)palladium and dichlorobis(triphenylphosphine)palladium. The amount of the catalyst is generally 0.001 to 0.5 molar equivalents, preferably 0.01 to 0.2 molar equivalents to the compound represented by the formula (IV). Further, in the reaction using the compound represented by the formula (V-a), a quaternary ammonium salt is preferably added to the reaction system. Examples of the quaternary ammonium salt include tetrabutylammonium bromide and the like.

The reaction temperature of the reaction using the compound represented by the formula (V-a) is generally at 20 to 180° C., preferably at 60 to 150° C. The reaction time of the reaction using the compound represented by the formula (V-a) is generally from 30 minutes to 100 hours.

The completion of the reaction can be confirmed by an analytical means such as thin layer chromatography, high performance liquid chromatography or the like after sampling a part of a reaction mixture. After the completion of the reaction, the compound represented by the formula (II) can be isolated, for example, by mixing the reaction mixture with water followed by extraction with an organic solvent, and then drying and concentrating the resulting organic layer.

The reaction using the compound represented by the formula (V-b) is performed in a solvent. Examples of the solvent include aromatic hydrocarbons such as benzene and toluene; ethers such as diethyl ether, diisopropyl ether, dioxane, tetrahydrofuran and dimethoxyethane; and a mixture thereof.

The reaction using the compound represented by the formula (V-b) is performed in the presence of a catalyst. Examples of the catalyst include nickel catalysts such as dichlorobis(1,3-diphenylphosphino)propane nickel and dichlorobis(triphenylphosphine)nickel; and palladium catalysts such as tetrakis(triphenylphosphine)palladium and dichlorobis(triphenylphosphine)palladium. The amount of the catalyst is generally 0.001 to 0.5 molar equivalents, preferably 0.01 to 0.2 molar equivalents to the compound represented by the formula (IV).

The reaction temperature of the reaction using the compound represented by the formula (V-b) is generally at −80 to 180° C., preferably at −30 to 150° C. The reaction time of the reaction using the compound represented by the formula (V-b) is generally from 30 minutes to 100 hours.

The completion of the reaction can be confirmed by an analytical means such as thin layer chromatography, high performance liquid chromatography or the like after sampling a part of a reaction mixture. After the completion of the reaction, the compound represented by the formula (II) can be isolated, for example, by mixing the reaction mixture with water followed by extraction with an organic solvent, and then drying and concentrating the resulting organic layer.

The reaction using the compound represented by the formula (V-c) is performed in a solvent. Examples of the solvent include aromatic hydrocarbons such as benzene and toluene; ethers such as diethyl ether, diisopropyl ether, dioxane, tetrahydrofuran and dimethoxyethane; halogenated hydrocarbons such as chloroform, 1,2-dichloroethane, etc.; amides such as dimethylformamide and dimethylacetamide; and a mixture thereof.

The reaction using the compound represented by the formula (V-c) is performed in the presence of a catalyst. Examples of the catalyst include palladium catalysts such as tetrakis(triphenylphosphine)palladium, and dichlorobis(triphenylphosphine)palladium. The amount of the catalyst is generally 0.001 to 0.5 molar equivalents, preferably 0.01 to 0.2 molar equivalents to the compound represented by the formula (IV).

The reaction temperature of the reaction using the compound represented by the formula (V-c) is generally at −80 to 180° C., preferably at −30 to 150° C. The reaction time of the reaction using the compound represented by the formula (V-c) is generally from 30 minutes to 100 hours.

The completion of the reaction can be confirmed by an analytical means such as thin layer chromatography, high performance liquid chromatography or the like after sampling a part of a reaction mixture. After the completion of the reaction, the compound represented by the formula (II) can be isolated, for example, by mixing the reaction mixture with water followed by extraction with an organic solvent, and then drying and concentrating the resulting organic layer.

The compound represented by the formula (II) can be prepared, for example, by a similar method to that described in Tetrahedron, Vol. 57, pp. 1323-1330 (2001).

The organometallic reagent represented by the formula (V-a), (V-b) or (V-c) is a known compound, or can be prepared from a known compound in accordance with a known method.

The compound represented by the formula (IV) is a known compound, or can be prepared from a known compound, for example, by a method described in J. Heterocycl. Chem., Vol. 33, pp. 1579-1582 (1996) or a similar method thereto.

Reference Preparation Method 2

The compound represented by the formula (VI) can be prepared, for example, by the following method:

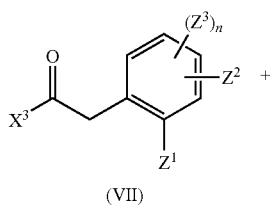

(VII)

-continued

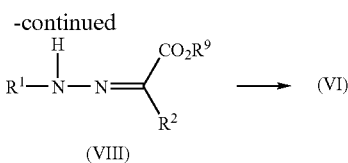

wherein X³ represents a halogen atom (for example, a chlorine atom, a bromine atom, or an iodine atom), and $R^1$, $R^2$, $R^9$, $Z^1$, $Z^2$, $Z^3$ and n are as defined above.

The reaction is generally performed in a solvent. Examples of the solvent include nitriles such as acetonitrile; ketones such as acetone; aromatic hydrocarbons such as benzene and toluene; ethers such as diethyl ether, diisopropyl ether, dioxane, tetrahydrofuran and dimethoxyethane; halogenated hydrocarbons such as dichloromethane, chloroform and 1,2-dichloroethane; amides such as dimethylformamide and dimethylacetoamide; sulfones such as sulfolane; and a mixture thereof.

The reaction is generally performed by reacting a compound represented by the formula (VII) with a compound represented by the formula (VIII) in the presence of a base. Examples of the base in the reaction include organic bases such as triethylamine, tripropylamine, pyridine, dimethylaminopyridine, 1,8-diazabicyclo[5.4.0]-7-undecene and 1,4-diazabicyclo[2.2.2]octane; and inorganic bases such as sodium hydroxide, potassium hydroxide, calcium hydroxide, sodium carbonate, potassium carbonate, sodium hydrogen carbonate, calcium carbonate and sodium hydride.

In the reaction, the compound represented by the formula (VIII) is generally used in an amount of 1 molar equivalent or more, preferably 1 to 3 molar equivalents to the compound represented by the formula (VII). The amount of the base used is generally 0.5 to 10 molar equivalents, preferably 1 to 5 molar equivalents to the compound represented by the formula (VII).

The reaction temperature is generally at −30 to 180° C., preferably at −10 to 50° C. The reaction time is generally from 10 minutes to 30 hours.

The completion of the reaction can be confirmed by an analytical means such as thin layer chromatography, high performance liquid chromatography or the like after sampling a part of a reaction mixture. After the completion of the reaction, the compound represented by the formula (VI) can be isolated, for example, by mixing the reaction mixture with water followed by extraction with an organic solvent, and then drying and concentrating the resulting organic layer.

The compound represented by the formula (VII) can be prepared by reacting a compound represented by the formula (IX):

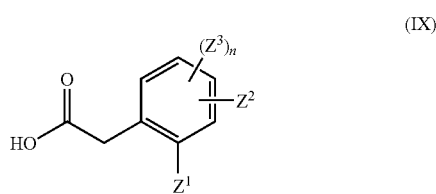

wherein $Z^1$, $Z^2$, $Z^3$ and n are as defined above, with a halogenating agent (for example, thionyl chloride, thionyl bromide, phosphorus oxychloride or oxalyl chloride).

The compound represented by the formula (IX) is a known compound, or can be prepared from a known compound, for example, by a method described in WO96/25395, WO96/35664, WO97/02243, WO99/43649, WO2001/017973, WO2004/065366, WO2004/080962, WO2005/016873, WO2005/044796, WO2005/092897 or WO2006/056281, or a similar method thereto.

Examples of the compound represented by the formula (IX) include 4-chloro-2,6-diethylphenylacetic acid, 4-bromo-2,6-diethylphenylacetic acid, 4-cyano-2,6-diethylphenylacetic acid, 2,6-diethyl-4-methoxyphenylacetic acid, 2,6-diethyl-4-phenylphenylacetic acid, 4-(4-chlorophenyl)-2,6-diethylphenylacetic acid, 2,6-diethyl-4-(4-methylphenyl)phenylacetic acid, 2,6-diethyl-4-ethynylphenylacetic acid, 2,6-diethyl-4-nitrophenylacetic acid, 2-cyano-4,6-dimethylphenylacetic acid, 2-cyano-6-ethyl-4-methylphenylacetic acid, 2,4-dichloro-6-methylphenylacetic acid, 2-chloro-4,6-dimethylphenylacetic acid, 2-chloro-6-ethyl-4-methylphenylacetic acid, 2,4-dichloro-6-ethylphenylacetic acid, 2-bromo-6-ethyl-4-methylphenylacetic acid, 4-chloro-2-ethyl-6-methoxyphenylacetic acid, 2-chloro-6-methoxy-4-methylphenylacetic acid, 2-ethyl-6-methoxy-4-methylphenylacetic acid, 2-ethyl-6-ethynyl-4-phenylphenylacetic acid, 2-chloro-6-ethyl-4-phenylphenylacetic acid, 2-ethyl-6-methoxy-4-phenylphenylacetic acid, 2,6-diethyl-4-trifluoromethylphenylacetic acid, 2,6-diethyl-4-trifluoromethoxyphenylacetic acid, 2-ethyl-6-ethynyl-4-methylphenylacetic acid, 2-chloro-6-ethyl-4-methoxyphenylacetic acid, 2-cyclopropyl-6-ethyl-4-methylphenylacetic acid, 4-cyclopropyl-2,6-diethylphenylacetic acid, 5-(4-chlorophenyl)-2-methylphenylacetic acid, 5-(4-fluorophenyl)-2-methylphenylacetic acid, 2-bromo-4,6-dimethylphenylacetic acid, 2-methoxy-4,6-dimethylphenylacetic acid and 2-ethynyl-4,6-dimethylphenylacetic acid.

The compound represented by the formula (VIII) is a known compound, or can be prepared from a known compound.

Each compound prepared by the Reference Preparation Methods 1 to 2 may be also isolated and/or purified by other known methods, such as concentration, concentration under reduced pressure, extraction, dissolution in different solvents, crystallization, recrystallization, chromatography and the like.

Examples of the compound represented by the formula (II) include the following compounds.

A compound represented by the formula (II), wherein n is 1, 2 or 3.

A compound represented by the formula (II), wherein $Z^2$ is attached to the 4- or 6-position on the benzene ring.

A compound represented by the formula (II), wherein n is 1, and $Z^2$ and $Z^3$ are respectively attached to the 4- and 6-positions or the 6- and 4-positions on the benzene ring.

A compound represented by the formula (II), wherein $R^1$ is a $C_{1-3}$ alkyl group or a $(C_{1-3}$ alkyloxy$)C_{1-3}$ alkyl group.

A compound represented by the formula (II), wherein $R^2$ is a hydrogen atom or a $C_{1-3}$ alkyl group.

A compound represented by the formula (II), wherein $R^2$ is a hydrogen atom or a methyl group.

A compound represented by the formula (II), wherein $Z^1$ is a $C_{1-3}$ alkyl group, $Z^2$ is a $C_{3-6}$ cycloalkyl group, a $C_{2-3}$ alkynyl group, a $C_{1-3}$ alkyloxy group, a $C_{1-3}$ haloalkyl group, a $C_{1-3}$ haloalkyloxy group, a halogen atom, a cyano group, a nitro group, or phenyl group which may be substituted with at least one group selected from the group consisting of a halogen atom and a $C_{1-3}$ alkyl group, and $Z^3$ is a $C_{1-3}$ alkyl group, a $C_{3-6}$ cycloalkyl group, a $C_{2-3}$ alkynyl group, a $C_{1-3}$ alkyloxy group or a halogen atom.

A compound represented by the formula (II), wherein $R^1$ is a $C_{1-3}$ alkyl group or a $(C_{1-3}$ alkyloxy$)C_{1-3}$ alkyl group, and $R^2$ is a hydrogen atom or a methyl group.

A compound represented by the formula (II), wherein $R^1$ is a $C_{1-3}$ alkyl group or a $(C_{1-3}$ alkyloxy$)C_{1-3}$ alkyl group, $R^2$ is a hydrogen atom or a $C_{1-3}$ alkyl group, n is 1, $Z^2$ and $Z^3$ are respectively attached to the 4- and 6-positions or the 6- and 4-positions on the benzene ring, $Z^1$ is a $C_{1-6}$ alkyl group (more preferably a $C_{1-3}$ alkyl group), $Z^2$ is a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group), a $C_{1-6}$ haloalkyl group (more preferably a $C_{1-3}$ haloalkyl group), a $C_{1-6}$ haloalkyloxy group (more preferably a $C_{1-3}$ haloalkyloxy group), a halogen atom, a cyano group, a nitro group, or a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group), and $Z^3$ is a $C_{1-6}$ alkyl group (more preferably a $C_{1-3}$ alkyl group), a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group) or a halogen atom.

A compound represented by the formula (II), wherein $R^1$ is a $C_{1-3}$ alkyl group or a $(C_{1-3}$ alkyloxy$)C_{1-3}$ alkyl group, $R^2$ is a hydrogen atom or a methyl group, n is 1, $Z^2$ and $Z^3$ are respectively attached to the 4- and 6-positions or the b- and 4-positions on the benzene ring, $Z^1$ is a $C_{1-6}$ alkyl group (more preferably a $C_{1-3}$ alkyl group), $Z^2$ is a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group), a $C_{1-6}$ haloalkyl group (more preferably a $C_{1-3}$ haloalkyl group), a $C_{1-6}$ haloalkyloxy group (more preferably a $C_{1-3}$ haloalkyloxy group), a halogen atom, a cyano group, a nitro group, or a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group), and $Z^3$ is a $C_{1-6}$ alkyl group (more preferably a $C_{1-3}$ alkyl group), a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group) or a halogen atom.

A compound represented by the formula (II), wherein n is 0, and $Z^2$ is attached to the 5-position on the benzene ring.

A compound represented by the formula (II), wherein $R^1$ is a $C_{1-3}$ alkyl group or a $(C_{1-3}$ alkyloxy$)C_{1-3}$ alkyl group, $R^2$ is a hydrogen atom or a $C_{1-3}$ alkyl group, n is 0, $Z^2$ is attached to the 5-position on the benzene ring, $Z^1$ is a $C_{1-6}$ alkyl group (more preferably a $C_{1-3}$ alkyl group), and $Z^2$ is a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group).

A compound represented by the formula (II), wherein $R^1$ is a $C_{1-3}$ alkyl group or a $(C_{1-3}$ alkyloxy$)C_{1-3}$ alkyl group, $R^2$ is a hydrogen atom or a methyl group, n is 0, $Z^2$ is attached to the 5-position on the benzene ring, $Z^1$ is a $C_{1-6}$ alkyl group (more preferably a $C_{1-3}$ alkyl group), and $Z^2$ is a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group).

Examples of the compound represented by the formula (VI) include the following compounds.

A compound represented by the formula (VI), wherein n is 1, 2 or 3.

A compound represented by the formula (VI), wherein $Z^2$ is attached to the 4- or 6 position on the benzene ring.

A compound represented by the formula (VI), wherein n is 1, and $Z^2$ and $Z^3$ are respectively attached to the 4- and 6-positions or the 6- and 4-positions on the benzene ring.

A compound represented by the formula (VI), wherein $R^1$ is a $C_{1-3}$ alkyl group or a $(C_{1-3}$ alkyloxy$)C_{1-3}$ alkyl group.

A compound represented by the formula (VI), wherein $R^2$ is a $C_{1-6}$ alkyl group.

A compound represented by the formula (VI), wherein $R^2$ is a hydrogen atom or a $C_{1-3}$ alkyl group.

A compound represented by the formula (VI), wherein $R^2$ is a $C_{1-3}$ alkyl group.

A compound represented by the formula (VI), wherein $R^2$ is a hydrogen atom or a methyl group.

A compound represented by the formula (VI), wherein $R^2$ is a methyl group.

A compound represented by the formula (VI), wherein $Z^1$ is a $C_{1-3}$ alkyl group, $Z^2$ is a $C_{3-6}$ cycloalkyl group, a $C_{2-3}$ alkynyl group, a $C_{1-3}$ alkyloxy group, a $C_{1-3}$ haloalkyl group, a $C_{1-3}$ haloalkyloxy group, a halogen atom, a cyano group, a nitro group, or a phenyl group which may be substituted with at least one group selected from the group consisting of a halogen atom and a $C_{1-3}$ alkyl group, and $Z^3$ is a $C_{1-3}$ alkyl group, a $C_{3-6}$ cycloalkyl group, a $C_{2-3}$ alkynyl group, a $C_{1-3}$ alkyloxy group or a halogen atom.

A compound represented by the formula (VI), wherein $R^1$ is a $C_{1-3}$ alkyl group or a $(C_{1-3}$ alkyloxy$)C_{1-3}$ alkyl group, and $R^2$ is a hydrogen atom or a methyl group.

A compound represented by the formula (VI), wherein $R^1$ is a $C_{1-3}$ alkyl group or a $(C_{1-3}$ alkyloxy$)C_{1-3}$ alkyl group, $R^2$ is a hydrogen atom or a $C_{1-3}$ alkyl group, n is 1, $Z^2$ and $Z^3$ are respectively attached to the 4- and 6-positions or the 6- and 4-positions on the benzene ring, $Z^1$ is a $C_{1-6}$ alkyl group (more preferably a $C_{1-3}$ alkyl group), $Z^2$ is a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group), a $C_{1-6}$ haloalkyl group (more preferably a $C_{1-3}$ haloalkyl group), a $C_{1-6}$ haloalkyloxy group (more preferably a $C_{1-3}$ haloalkyloxy group), a halogen atom, a cyano group, a nitro group, or a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group), and $Z^3$ is a $C_{1-6}$ alkyl group (more preferably a $C_{1-3}$ alkyl group), a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group) or a halogen atom.

A compound represented by the formula (VI), wherein $R^1$ is a $C_{1-3}$ alkyl group or a $(C_{1-3}$ alkyloxy$)C_{1-3}$ alkyl group, $R^2$ is a hydrogen atom or a methyl group, n is 1, $Z^2$ and $Z^3$ are respectively attached to the 4- and 6-positions or the b- and 4-positions on the benzene ring, $Z^1$ is a $C_{1-6}$ alkyl group (more preferably a $C_{1-3}$ alkyl group), $Z^2$ is a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group), a $C_{1-6}$ haloalkyl group (more preferably a $C_{1-3}$ haloalkyl group), a $C_{1-6}$ haloalkyloxy group (more preferably a $C_{1-3}$ haloalkyloxy group), a halogen atom, a cyano group, a nitro group, or a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group), and $Z^3$ is a $C_{1-6}$ alkyl group (more preferably a $C_{1-3}$ alkyl group), a $C_{3-8}$ cycloalkyl group (more preferably a $C_{3-6}$ cycloalkyl group), a $C_{2-6}$ alkynyl group (more preferably a $C_{2-3}$ alkynyl group), a $C_{1-6}$ alkyloxy group (more preferably a $C_{1-3}$ alkyloxy group) or a halogen atom.

A compound represented by the formula (VI), wherein n is 0, and $Z^2$ is attached to the 5-position on the benzene ring.

A compound represented by the formula (VI), wherein $R^1$ is a $C_{1-3}$ alkyl group or a $(C_{1-3}$ alkyloxy$)C_{1-3}$ alkyl group, $R^2$ is a hydrogen atom or a $C_{1-3}$ alkyl group, n is 0, $Z^2$ is attached to the 5-position on the benzene ring, $Z^1$ is a $C_{1-6}$ alkyl group (more preferably a $C_{1-3}$ alkyl group), and $Z^2$ is a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group).

A compound represented by the formula (VI), wherein $R^1$ is a $C_{1-3}$ alkyl group or a $(C_{1-3}$ alkyloxy$)C_{1-3}$ alkyl group, is a hydrogen atom or a methyl group, n is 0, $Z^2$ is attached to the 5-position on the benzene ring, $Z^1$ is a $C_{1-6}$ alkyl group (more preferably a $C_{1-3}$ alkyl group), and $Z^2$ is a $C_{6-10}$ aryl group (more preferably a phenyl group) which may be substituted with at least one group selected from the group consisting of a halogen atom and a $C_{1-6}$ alkyl group (more preferably a $C_{1-3}$ alkyl group).

EXAMPLES

The present invention will be further specifically illustrated by the following Examples, Reference examples, Formulation examples and Test examples, however the present invention is not limited to these examples.

In Examples and Reference examples, room temperature means usually 10 to 30° C. $^1$H NMR means proton nuclear magnetic resonance. Tetramethylsilane was used as an internal standard, and chemical shift (δ) was shown as ppm.

Abbreviations used in Examples and Reference examples have the following meanings.
$CDCl_3$: chloroform-d, s: singlet, d: doublet, t: triplet, q: quartet, m: multiplet, br.: broad, J: coupling constant, Me: methyl, Et: ethyl, c-Pr: cyclopropyl, Ph: phenyl, 4-Me-Ph: 4-methylphenyl, 4-Cl-Ph: 4-chlorophenyl.

Example 1

4-(4-Chloro-2,6-diethylphenyl)-5-hydroxy-2,6-dimethyl-3(2H)-pyridazinone (compound I-a-2)

A solution of 0.55 g of potassium tert-butoxide in 20 mL of tetrahydrofuran was stirred at 36 to 38° C. under nitrogen atmosphere. To the solution was added dropwise a solution of 0.79 g of ethyl 2-[2-(4-chloro-2,6-diethylphenylacetyl)-2-methylhydrazono]propanoate (compound VI-2) in 15 mL of toluene over about 20 minutes. The mixture was further stirred at the same temperature for 10 minutes. Then, the reaction mixture was concentrated under reduced pressure. To the residue was added 20 mL of ice water, followed by extraction with tert-butyl methyl ether (20 mL×2). An aqueous layer was acidified by an addition of 0.6 g of 35% hydrochloric acid, followed by extraction with ethyl acetate (20 mL×2). The ethyl acetate extracts were combined, washed with an aqueous saturated sodium chloride solution (20 mL×2), dried over anhydrous magnesium sulfate, and then concentrated under reduced pressure. The residue was subjected to silica gel chromatography (ethyl acetate:hexane=1:4) to give 0.1 g of a solid. The solid was washed with an ethyl acetate-hexane mixture solvent (1:10) and air dried to give 0.07 g of the title compound as a white powder.

Compounds of the present invention represented by the formula (I-a) were prepared by the procedure similar to Example 1 and are shown in Table 1, together with the compound I-a-2.

The compound represented by the formula (I-a):

TABLE 1

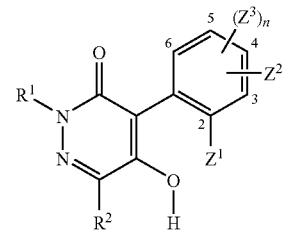

(I-a)

| No. | $R^1$ | $R^2$ | $Z^1$ | $Z^2$ | $(Z^3)_n$ | Melting point/° C. |
|---|---|---|---|---|---|---|
| I-a-1 | Me | Me | Et | 4-Ph | 6-Et | 231-232 |
| I-a-2 | Me | Me | Et | 4-Cl | 6-Et | 234-235 |
| I-a-3 | Me | Me | Et | 4-OMe | 6-Et | 205-206 |
| I-a-4 | Me | Me | Et | 4-Br | 6-Et | 251-252 |
| I-a-5 | Me | Me | Et | 4-CN | 6-Et | 243-245 |
| I-a-6 | Me | Me | Et | 4-$CF_3$ | 6-Et | 270-271 |
| I-a-7 | Me | Me | Et | 4-$OCF_3$ | 6-Et | 230-231 |
| I-a-8 | Me | Me | Et | 4-(c-Pr) | 6-Et | 217-218 |
| I-a-9 | Me | Me | Et | 4-(4-Me—Ph) | 6-Et | 214-215 |
| I-a-10 | Me | Me | Me | 5-(4-Cl—Ph) | — | 234-236 |
| I-a-11 | Me | Me | Me | 6-Br | 4-Me | 220-221 |

Example 2

5-Acetoxy-4-(2,6-diethyl-4-phenylphenyl)-2,6-dimethyl-3(2H)-pyridazinone (compound I-b-1)

To a solution of 0.04 g of the compound I-a-1 (prepared by the procedure similar to Example 1) in 10 mL of tetrahydrofuran were added 0.03 g of triethylamine, 0.02 g of acetic anhydride and then 2 mg of 4-dimethylaminopyridine. The mixture was stirred at room temperature for 9.5 hours. The reaction solution was concentrated under reduced pressure. To the residue was added 10 mL of ice water, followed by extraction with ethyl acetate (10 mL×3). The extracts were combined, washed with an aqueous saturated sodium chloride solution (10 mL×2), dried over anhydrous magnesium sulfate, and then concentrated under reduced pressure. The residue was subjected to silica gel chromatography (ethyl acetate:hexane=1:6) to give 0.05 g of a solid. The solid was washed with cold hexane and air dried to give 0.025 g of the title compound as a white powder.

Compounds of the present invention represented by the formula (I-b) were prepared by the procedure similar to Example 2 and are shown in Table 2, together with the compound I-b-1.

The compound represented by the formula (I-b):

TABLE 2

(I-b)

| No. | $R^1$ | $R^2$ | $Z^1$ | $Z^2$ | $(Z^3)_n$ | $G^3$ | Melting point/° C. |
|---|---|---|---|---|---|---|---|
| I-b-1 | Me | Me | Et | 4-Ph | 6-Et | COMe | 125-127 |
| I-b-2 | Me | Me | Et | 4-Br | 6-Et | $CO_2Me$ | 125-127 |
| I-b-3 | Me | Me | Et | 4-(c-Pr) | 6-Et | $CO_2Me$ | 102-103 |
| I-b-4 | Me | Me | Et | 4-(4-Me—Ph) | 6-Et | COMe | 153-155 |
| I-b-5 | Me | Me | Me | 5-(4-Cl—Ph) | — | COMe | 153-154 |
| I-b-6 | Me | Me | Me | 6-Br | 4-Me | $CO_2Me$ | 114-115 |

Example 3

4-(2,6-Diethyl-4-ethynylphenyl)-5-hydroxy-2,6-dimethyl-3(2H)-pyridazinone (compound I-a-20)

A dry nitrogen gas was blown into a solution of 0.49 g of the compound I-b-2 (prepared by the procedure similar to Example 2) and 0.56 g of tributyl(trimethylsilylethynyl)tin in 10 mL of toluene for 70 minutes. To the reaction solution was added 0.08 g of tetrakis(triphenylphosphine) palladium. The mixture was stirred at 100 to 110° C. under dry nitrogen atmosphere for 5 hours. After cooling, insoluble matters was filtered out from the reaction mixture. The filtrate was concentrated under reduced pressure. The residue was subjected to silica gel chromatography (ethyl acetate:hexane=1:8) to give 0.43 g of 4-(2,6-diethyl-4-trimethylsilylethynylphenyl)-5-methoxycarbonyloxy-2,6-dimethyl-3(2H)-pyridazinone as a yellow resin.

$^1$H NMR (CDCl$_3$) δ ppm: 0.26 (9H, s), 1.12 (6H, t, J=7.6 Hz), 2.29 (3H, s), 2.26-2.43 (4H, m), 3.68 (3H, s), 3.81 (3H, s), 7.27 (2H, s).

The product was dissolved in 15 mL of ethanol and stirred under ice cooling, and thereto a solution of 0.13 g of 95.0% sodium hydroxide in 2 mL of water was added. The reaction solution was stirred at room temperature for 22.5 hours, and then concentrated under reduced pressure. To the residue was added 20 mL of ice water, followed by extraction with tert-butyl methyl ether (20 mL). An aqueous layer was acidified by an addition of 1.5 mL of 3N hydrochloric acid, followed by extraction with ethyl acetate (20 mL, 10 mL). The ethyl acetate extracts were combined, washed with an aqueous saturated sodium chloride solution (20 mL×2), dried over anhydrous magnesium sulfate, and then concentrated under reduced pressure. The residue was subjected to silica gel chromatography (ethyl acetate:hexane=1:3) to give 0.15 g of a solid. The solid was washed with an ethyl acetate-hexane mixture solvent (1:10) and air dried to give 0.13 g of the title compound as a white powder. m.p. 216-217° C.

Example 4

4-(2-Ethynyl-4,6-dimethylphenyl)-5-hydroxy-2,6-dimethyl-3(2H)-pyridazinone (compound I-a-21)

From the compound I-b-6 (prepared by the procedure similar to Example 2), 4-(4,6-dimethyl-2-trimethylsilylethy-nylphenyl)-5-methoxycarbonyloxy-2,6-dimethyl-3(2H)-pyridazinone was prepared as a yellow brown solid by the procedure similar to Example 3.

$^1$H NMR (CDCl$_3$) δ ppm: 0.07 (9H, s), 2.13 (3H, s), 2.29 (6H, s), 3.69 (3H, s), 3.81 (3H, s), 7.03 (1H, s), 7.19 (1H, s).

Furthermore, from this product, the title compound was prepared as a white powder by the procedure similar to Example 3. m.p. 179-181° C.

A typical preparation example of the compound represented by the formula (VI) is shown in Reference Example 1.

Reference Example 1

Ethyl 2-[2-(4-chloro-2,6-diethylphenylacetyl)-2-methylhydrazono]propanoate (compound VI-2)

To a solution of 1.1 g of ethyl 2-(methylhydrazono)propanoate in 20 mL of acetonitrile was added 0.68 g of potassium carbonate. The mixture was stirred under ice cooling. To the mixture was added dropwise a solution of 1.26 g of 4-chloro-2,6-diethylphenylacetyl chloride in 8 mL of acetonitrile over about 10 minutes. The mixture was further stirred at room temperature for 3 hours. Then, the reaction mixture was concentrated under reduced pressure. To the residue was added 20 mL of ice water, followed by extraction with ethyl acetate (20 mL, 10 mL×2). The extracts were combined, washed with an aqueous saturated sodium chloride solution (20 mL×2), dried over anhydrous magnesium sulfate, and then concentrated under reduced pressure. The residue was subjected to basic alumina column chromatography (ethyl acetate:hexane=1:6) to give 1.2 g of a light yellow solid. The solid was washed with cold hexane and air dried to give 0.79 g of the title compound as a white powder.

Compounds represented by the formula (VI) were prepared by the procedure similar to Reference Example 1, and are shown in Table 3, together with the compound VI-2. The compound represented by the formula (VI):

TABLE 3

(VI)

| No. | $R^1$ | $R^2$ | $Z^1$ | $Z^2$ | $(Z^3)_n$ | $R^9$ | Melting point/° C. |
|---|---|---|---|---|---|---|---|
| VI-1 | Me | Me | Et | 4-Ph | 6-Et | Et | 75-78 |
| VI-2 | Me | Me | Et | 4-Cl | 6-Et | Et | 85-89 |
| VI-3 | Me | Me | Et | 4-OMe | 6-Et | Et | * |
| VI-4 | Me | Me | Et | 4-Br | 6-Et | Et | 80-84 |
| VI-5 | Me | Me | Et | 4-CN | 6-Et | Et | * |
| VI-6 | Me | Me | Et | 4-CF$_3$ | 6-Et | Et | 90-91 |
| VI-7 | Me | Me | Et | 4-OCF$_3$ | 6-Et | Et | 75-76 |
| VI-8 | Me | Me | Et | 4-(c-Pr) | 6-Et | Et | * |
| VI-9 | Me | Me | Et | 4-(4-Me—Ph) | 6-Et | Et | * |
| VI-10 | Me | Me | Me | 5-(4-Cl—Ph) | — | Et | * |
| VI-11 | Me | Me | Me | 6-Br | 4-Me | Et | * |

Regarding the compounds marked with asterisk (*) in the column of melting point of Table 3, $^1$H NMR data are shown below.

Compound VI-3:

$^1$H NMR (CDCl$_3$) δ ppm: 1.18 (6H, J=7.6 Hz), 1.36 (3H, t, J=7.1 Hz), 2.31 (3H, br.s), 2.57 (4H, q, J=7.4 Hz), 3.40 (3H, br.s), 3.79 (3H, s), 4.01 (2H, br.s), 4.33 (2H, q, J=7.1 Hz), 6.64 (2H, s).

Compound VI-5:

$^1$H NMR (CDCl$_3$) δ ppm: 1.20 (6H, t, J=7.6 Hz), 1.37 (3H, t, J=7.1 Hz), 2.34 (3H, s), 2.61 (4H, q, J=7.5 Hz), 3.41 (3H, s), 4.12 (2H, s), 4.34 (2H, q, J=7.1 Hz), 7.36 (2H, s).

Compound VI-8:

$^1$H NMR (CDCl$_3$) δ ppm: 0.62-0.73 (2H, m), 0.85-0.95 (2H, m), 1.17 (6H, t, J=7.6 Hz), 1.35 (3H, t, J=7.1 Hz), 1.79-1.90 (1H, m), 2.31 (3H, br.s), 2.55 (4H, q, J=7.6 Hz), 3.39 (3H, br.s), 4.04 (2H, br.s), 4.32 (2H, q, J=7.1 Hz), 6.78 (2H, s).

Compound VI-9:

$^1$H NMR (CDCl$_3$) δ ppm: 1.23 (6H, t, J=7.6 Hz), 1.36 (3H, t, J=7.2 Hz), 2.33 (3H, br.s), 2.39 (3H, s), 2.65 (4H, q, J=7.6 Hz), 3.42 (3H, br.s), 4.12 (2H, br.s), 4.33 (2H, q, J=7.1 Hz), 7.23 (2H, d, J=8.0 Hz), 7.28 (2H, s), 7.49 (2H, d, J=8.3 Hz).

Compound VI-10:

$^1$H NMR (CDCl$_3$) δ ppm: 1.33 (3H, t, J=7.2 Hz), 2.21 (3H, s), 2.35 (3H, s), 3.37 (3H, s), 4.06 (2H, br.s), 4.28 (2H, q, J=7.1 Hz), 7.22 (1H, d, J=7.8 Hz), 7.30~7.40 (3H, m), 7.43 (1H, br.s), 7.47 (2H, d, J=8.3 Hz).

Compound VI-11:

$^1$H NMR (CDCl$_3$) δ ppm: 1.37 (3H, t, J=7.1 Hz), 2.20-2.39 (9H, m), 3.40 (3H, br.s), 4.16 (2H, br.s), 4.33 (2H, q, J=7.2 Hz), 6.94 (1H, br.s), 7.25 (1H, br.s).

Formulation Example 1

Emulsifiable Concentrate

| | |
|---|---|
| Compound I-a-1 | 20% by weight |
| Polyoxyethylene alkyl ether | 5% by weight |
| Dimethylformamide | 18% by weight |
| Xylene | 57% by weight |

The above listed ingredients are mixed to obtain an emulsifiable concentrate. The prepared emulsifiable concentrate is diluted with water appropriately before use.

Each of the compounds I-a-2 to I-a-11, I-a-20, I-a-21 and I-b-1 to I-b-6 is used instead of the compound I-a-1 to obtain an emulsifiable concentrate of each compound.

Formulation Example 2

Wettable Powder

| | |
|---|---|
| Compound I-b-1 | 50% by weight |
| Sodium lignin sulfonate | 5% by weight |
| Polyoxyethylene alkyl ether | 5% by weight |
| White carbon | 5% by weight |
| Clay | 35% by weight |

The above listed ingredients are pulverized and mixed to obtain a wettable powder. The prepared wettable powder, is diluted with water appropriately before use.

Each of the compounds I-a-1 to I-a-11, I-a-20, I-a-21 and I-b-2 to I-b-6 is used instead of the compound I-b-1 to obtain a wettable powder of each compound.

Formulation Example 3

Granule

| | |
|---|---|
| Compound I-a-2 | 1.5% by weight |
| Sodium lignin sulfonate | 2% by weight |
| Talc | 40% by weight |
| Bentonite | 56.5% by weight |

The above listed ingredients are mixed, kneaded with water and then granulated to obtain a granule.

Each of the compounds I-a-1, I-a-3 to I-a-11, I-a-20, I-a-21 and I-b-1 to I-b-6 is used instead of the compound I-a-2 to obtain a granule of each compound.

Test Example 1

Post-Emergence Treatment Test in Dry Field

A plastic cup with a diameter of 8 cm and a depth of 6.5 cm was filled with commercially available soil. Seeds of *Lolium multiflorum* were sowed in the cup, covered with soil about 0.5 cm thick and then grown in a greenhouse. When the plants were grown in the first to second leaf stage, a diluted liquid formulation containing a prescribed amount of the compound I-a-2 was sprayed onto the whole plants uniformly. The diluted liquid formulation was prepared by dissolving a prescribed amount of the compound I-a-2 in a 2% solution of Tween 20 (polyoxyethylene sorbitan fatty acid ester, MP Biomedicals, Inc.) in dimethylformamide and then diluting the solution with deionized water. After the treatment, the plants were grown in a greenhouse. Twenty days after treatment, the controlling effect of the compound on *Lolium multiflorum* was visually evaluated. The effect was rated in 11 levels, from 0 to 10 (0 represents "no effect"; 10 represents "complete death"; and a state of the plant therebetween is rated in levels of 1 to 9).

The other compounds of the present invention, and Compound A described in J. Heterocycl. Chem., vol. 42, pp. 427-435 (2005) as a comparative example were similarly tested.

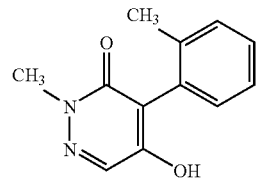 [SMILES: Cc1ccccc1-c1c(O)cnn(C)c1=O]

Comparative Example

Compound A

As a result, the compounds I-a-1, I-a-2, I-a-3, I-a-4, I-a-6, I-a-7, I-a-8, I-a-9, I-a-20, I-b-1 and I-b-4 showed an effect of 7 or more at a treatment amount of 250 g/ha. In contrast, Compound A showed an effect of 1 at a treatment amount of 500 g/ha.

Test Example 2

Pre-Emergence Treatment Test in Dry Field

A plastic container (32 cm×22 cm×8 cm in height) was filled with soil sterilized by steam. Seeds of *Apera spica-venti* were sowed in the container and covered with soil about 0.5 cm thick. Then, a diluted liquid formulation containing a prescribed amount of the compound I-a-1 was sprayed onto the soil surface uniformly. The diluted liquid formulation was prepared by the method similar to that in Test example 1. After the treatment, the plants were grown in a greenhouse. Three weeks after treatment, the controlling effect of the compound on Apera spica-venti was visually evaluated. The effect was rated in 11 levels, from 0 to 10 similarly to Test example 1.

The other compounds of the present invention and Compound A as a comparative example were similarly tested.

As a result, the compound I-a-1, I-a-4, I-a-6, I-a-7, I-a-8, I-a-9, I-a-10, I-a-20, I-b-3, I-b-4 and I-b-5 showed an effect of 8 or more at a treatment amount of 250 g/ha. The compound I-b-1 showed an effect of 8 or more at a treatment amount of 125 g/ha. In contrast, Compound A showed an effect of 1 at a treatment amount of 500 g/ha.

INDUSTRIAL APPLICABILITY

According to the present invention, weeds can be controlled by applying an effective amount of the compound of the present invention to the weeds or soil where the weeds are grown.

The invention claimed is:

1. A pyridazinone compound represented by the formula (I):

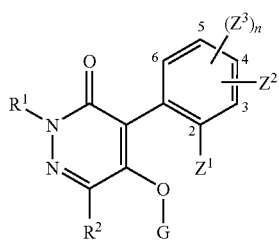

wherein
- $R^1$ represents a $C_{1-6}$ alkyl group or a $(C_{1-6}$ alkyloxy$)C_{1-6}$ alkyl group;
- $R^2$ represents a hydrogen atom or a $C_{1-6}$ alkyl group;
- G represents a hydrogen atom or a group represented by any one of the following formulas:

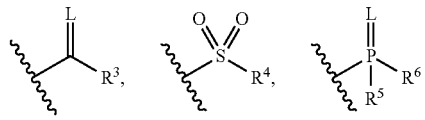

(wherein L represents an oxygen or sulfur atom,
- $R^3$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a $(C_{6-10}$ aryl$)C_{1-6}$ alkyl group, a $C_{1-6}$ alkyloxy group, a $C_{3-8}$ cycloalkyloxy group, a $C_{2-6}$ alkenyloxy group, a $C_{3-6}$ alkynyloxy group, a $C_{6-10}$ aryloxy group, a $(C_{6-10}$ aryl$)C_{1-6}$ alkyloxy group, a di($C_{1-6}$ alkyl)amino group, a di($C_{2-6}$ alkenyl)amino group, a $(C_{1-6}$ alkyl$)(C_{6-10}$ aryl$)$amino group or a 3- to 8-membered nitrogen-containing heterocyclic group,
- $R^4$ represents a $C_{1-6}$ alkyl group, a $C_{6-10}$ aryl group or a di($C_{1-6}$ alkyl)amino group, and
- $R^5$ and $R^6$ may be the same as or different from each other, and represent a $C_{1-6}$ alkyl group, a $C_{3-8}$ cycloalkyl group, a $C_{2-6}$ alkenyl group, a $C_{6-10}$ aryl group, a $C_{1-6}$ alkyloxy group, a $C_{3-8}$ cycloalkyloxy group, a $C_{6-10}$ aryloxy group, a $(C_{6-10}$ aryl$)C_{1-6}$ alkyloxy group, a $C_{1-6}$ alkylthio group or a di($C_{1-6}$ alkyl)amino group, wherein any group represented by $R^3$, $R^4$, $R^5$ and $R^6$ may be substituted with at least one halogen atom, and the $C_{3-8}$ cycloalkyl group, the $C_{6-10}$ aryl group, the aryl moiety of the $(C_{6-10}$ aryl$)C_{1-6}$ alkyl group, the $C_{3-8}$ cycloalkyloxy group, the $C_{6-10}$ aryloxy group, the aryl moiety of the $(C_{6-10}$ aryl$)C_{1-6}$ alkyloxy group, the aryl moiety of the $(C_{1-6}$ alkyl$)(C_{6-10}$ aryl$)$amino group and the 3- to 8-membered nitrogen-containing heterocyclic group may be substituted with at least one $C_{1-6}$ alkyl group);
- $Z^1$ represents a $C_{1-6}$ alkyl group or a $C_{1-6}$ alkyloxy group;
- $Z^2$ represents a $C_{3-8}$ cycloalkyl group, a $C_{2-6}$ alkynyl group, a $C_{1-6}$ alkyloxy group, a $C_{1-6}$ haloalkyl group, a $C_{1-6}$ haloalkyloxy group, a halogen atom, a $C_{6-10}$ aryl group, a 5- or 6-membered heteroaryl group, a cyano group or a nitro group, and
- $Z^3$ represents a $C_{1-6}$ alkyl group, a $C_{3-8}$ cycloalkyl group, a $C_{2-6}$ alkynyl group, a $C_{1-6}$ alkyloxy group, a $C_{1-6}$ haloalkyl group, a $C_{1-6}$ haloalkyloxy group, a halogen atom, a $C_{6-10}$ aryl group, a 5- or 6-membered heteroaryl group, a cyano group or a nitro group,
- wherein the $C_{3-8}$ cycloalkyl group, the $C_{6-10}$ aryl group and the 5- or 6-membered heteroaryl group represented by $Z^2$ and $Z^3$ may be substituted with at least one group selected from the group consisting of a halogen atom and a $C_{1-6}$ alkyl group; and
- n represents 0, 1, 2 or 3, and when n is 2 or 3, each of $Z^3$ may be the same as or different from each other.

2. The pyridazinone compound according to claim 1, wherein n is 1, 2 or 3.

3. The pyridazinone compound according to claim 1, wherein $Z^2$ is attached to the 4- or 6-position on the benzene ring with the numbered ring positions.

4. The pyridazinone compound according to claim 1, wherein n is 1, and $Z^2$ and $Z^3$ are respectively attached to the 4- and 6-positions or the 6- and 4-positions on the benzene ring with the numbered ring positions.

5. The pyridazinone compound according to claim 1, wherein $Z^1$ represents a $C_{1-3}$ alkyl group, $Z^2$ represents a $C_{3-6}$ cycloalkyl group, a $C_{2-3}$ alkynyl group, a $C_{1-3}$ alkyloxy group, a halogen atom, a cyano group, a nitro group, or a phenyl group which may be substituted with at least one group selected from the group consisting of a halogen atom and a $C_{1-3}$ alkyl group, and $Z^3$ represents a $C_{1-3}$ alkyl group, a $C_{3-6}$ cycloalkyl group, a $C_{2-3}$ alkynyl group, a $C_{1-3}$ alkyloxy group or a halogen atom.

6. The pyridazinone compound according to claim 1, wherein G represents a hydrogen atom or a group represented by any one of the following formulas:

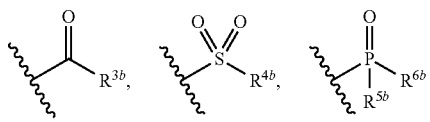

(wherein $R^{3b}$ represents a $C_{1-6}$ alkyl group, a $C_{3-8}$ cycloalkyl group, a $C_{2-6}$ alkenyl group, a $C_{2-6}$ alkynyl group, a $C_{6-10}$ aryl group, a $(C_{6-10}$ aryl$)C_{1-6}$ alkyl group, a $C_{1-6}$ alkyloxy group, a $C_{3-8}$ cycloalkyloxy group, a $C_{6-10}$ aryloxy group, a $(C_{6-10}$ aryl$)C_{1-6}$ alkyloxy group or a di($C_{1-6}$ alkyl)amino group, $R^{4b}$ represents a $C_{1-6}$ alkyl group or a $C_{6-10}$ aryl group, and $R^{5b}$ and $R^{6b}$ may be the same as or different from each other, and represent a $C_{1-6}$ alkyl group, a $C_{1-6}$ alkyloxy group, a $C_{6-10}$ aryloxy group or a $C_{1-6}$ alkylthio group, wherein any group represented by $R^{3b}$, $R^{4b}$, $R^{5b}$ and $R^{6b}$ may be substituted with at least one halogen atom, and the $C_{3-8}$ cycloalkyl group, the $C_{6-10}$ aryl group, the aryl moiety of the $(C_{6-10}$ aryl$)C_{1-6}$ alkyl group, the $C_{3-8}$ cycloalkyloxy group, the $C_{6-10}$ aryloxy group, and the aryl moiety of the $(C_{6-10}$ aryl$)C_{1-6}$ alkyloxy group may be substituted with at least one $C_{1-6}$ alkyl group).

7. The pyridazinone compound according to claim 1, wherein G represents a hydrogen atom or a group represented by any one of the following formulas:

(wherein $R^{3a}$ represents a $C_{1-6}$ alkyl group, a $C_{3-8}$ cycloalkyl group, a $C_{6-10}$ aryl group, a $C_{1-6}$ alkyloxy group or a di($C_{1-6}$ alkyl)amino group, and $R^{4a}$ represents a $C_{1-6}$ alkyl group, wherein any group represented by $R^{3a}$ and $R^{4a}$ may be substituted with at least one halogen atom, and the $C_{3-8}$ cycloalkyl group and the $C_{6-10}$ aryl group may be substituted with at least one $C_{1-6}$ alkyl group).

8. The pyridazinone compound according to claim 1, wherein $R^2$ is a hydrogen atom or a $C_{1-3}$ alkyl group.

9. The pyridazinone compound according to claim 1, wherein $R^2$ is a hydrogen atom or a methyl group.

10. The pyridazinone compound according to claim 1, wherein $R^1$ is a $C_{1-3}$ alkyl group or a $(C_{1-3}$ alkyloxy$)C_{1-3}$ alkyl group.

11. A comprising the pyridazinone compound according to claim 1 as an active ingredient.

\* \* \* \* \*